United States Patent [19]
Beckman et al.

[11] Patent Number: 5,872,257
[45] Date of Patent: Feb. 16, 1999

[54] FURTHER EXTRACTIONS OF METALS IN CARBON DIOXIDE AND CHELATING AGENTS THEREFOR

[75] Inventors: Eric J. Beckman, Edwood; Alan J. Russell, Wexford, both of Pa.

[73] Assignee: University of Pittsburgh, Pittsburgh, Pa.

[21] Appl. No.: 831,999

[22] Filed: Apr. 1, 1997

Related U.S. Application Data

[63] Continuation-in-part of Ser. No. 223,105, Apr. 1, 1994, Pat. No. 5,641,887.

[51] Int. Cl.$^6$ .................................................. C07D 401/06
[52] U.S. Cl. ........................ 546/336; 546/255; 546/262; 546/335; 526/247; 210/634; 544/272
[58] Field of Search .................................... 546/255, 262, 546/335, 336; 544/272; 526/247; 210/634

[56] References Cited

U.S. PATENT DOCUMENTS

| | | | |
|---|---|---|---|
| 4,031,038 | 6/1977 | Grinstead et al. | 546/262 |
| 4,741,831 | 5/1988 | Grinstead | 210/638 |
| 4,831,206 | 5/1989 | Zarchy | 585/737 |
| 5,114,689 | 5/1992 | Nagji | 423/230 |

OTHER PUBLICATIONS

"Separation of Metal Ions with Sodium Bis(trifluoroethyl)dithiocarbamate Chelation and Supercritical Fluid Chromatography" by K.E. Laintz et al., *Analytical Chemistry*, vol. 64, No. 3 (1992), pp. 311–315.

"Design and Synthesis of Highly $CO_2$–Soluble Surfactants and Chelating Agents" by T.A. Hoefling et al., *Fluid Phase Equilibria* 83 (1993) 203–212.

"Spectrophotometric Studies Cobalt(II) and Copper(II) Chelates of 2–Picolylamine" by T.M. Hseu et al., *J. Chin. Chem. Soc.*, 1974, 21(4) 211–21 (Eng.).

"Spectrophotometric Studies of Nickel(II) Chelate of 2–Picolylamine" by T.M. Hseu et al., *J. Chin. Chem. Soc.*, 1975, 22(4) 299–308 (Eng.).

"Lubricating Agent for Magnetic Recording Medium" by T. Idekura, C.A. 113:203657 (1990).

*Primary Examiner*—Ceila Chang
*Attorney, Agent, or Firm*—Conley, Rose & Tayon, P.C.

[57] ABSTRACT

The present invention provides a chelating agent suitable for forming coordinated complexes with a metal in liquid and supercritical carbon dioxide of covalently bonded (i) a chelating group selected from the group consisting of a dithio carbamate, a thiol group, and a picolyl amine group, (ii) a non-electron withdrawing spacer group selected from $(CH_2)_x$; and (iii) a $CO_2$-soluble functional group selected from $(CF_2CF_2O)_x$, $(CF_2O)_x$, $(CF_2)_x$, and $[CF_2(CF_3FO)]_x$. X is selected to be greater or equal to 3 and to minimize the electron withdrawing effect of the $CO_2$-soluble functional group and to achieve a chelating agent solubility of at least a $10^{-3}$ gm/gm $CO_2$. A solubility of at least $10^{-2}$ gm/gm $CO_2$ is attained at a temperature in the range of approximately 0° to 100° C. and a pressure of approximately 500 to 5000 psi.

20 Claims, 26 Drawing Sheets

Figure 1(f)

| Metal | Preferred CO$_2$-philic Groups | Chelating Head Group |
|---|---|---|
| Pb | Flouroether<br>Silicone<br>Flouroalkyl | ![structure: —N with three CH$_2$-pyridyl arms] |
| Hg | Flouroether<br>Flouroalkyl | ![structure: —NH—CH$_2$-pyridyl; and CH$_3$CH$_2$CH(SH)CH$_2$SH] |
| As | Flouroether<br>Flouroalkyl | —N−C(=S)−S$^\ominus$ ; —N(CH$_2$COOH)$_2$ |
| U | Flouroether<br>Flouroalkyl | —O−P(=O)(OH)−OH |
| Au | Flouroether<br>Flouroalkyl | CH$_3$CH$_2$CH(SH)CH$_2$SH |
| Ni | Flouroether<br>Flouroalkyl | ![structure: N with two CH$_2$-pyridyl arms] |
| Cu | Flouroether<br>Flouroalkyl | —N(CH$_2$COOH)$_2$ |

FE = Fluoroether such as Hexaflouropropylene oxide i)

ii)

iii)

iv)

Hydroxyethyl imino diacetic acid

FURTHER EXTRACTIONS OF METALS IN CARBON DIOXIDE AND CHELATING AGENTS THEREFOR

This is a continuation-in-part of Ser. No. 08/223,105, filed Apr. 1, 1994, now U.S. Pat. No. 5,641,887, entitled "Extraction of Metals in Carbon Dioxide and Chelating Agents Therefor."

FIELD OF THE INVENTION

The present invention relates to a method of further extractions of metals in carbon dioxide and also to chelating agents therefor, and especially to the extraction of metals in liquid or supercritical carbon dioxide using novel molecules comprising chelating agents derivatized with functional groups exhibiting suitable $CO_2$ solubility.

BACKGROUND OF THE INVENTION

As a result of their favorable properties, including variable solvent power and low viscosity, supercritical fluids have been employed in a variety of selective extraction processes. Whereas a number of common gases exhibit desirably low critical temperatures (below 100° C.), however, carbon dioxide is without question the most widely-used solvent in supercritical fluid science and technology. McHugh, M. A. and Krukonis, V. J., *Supercritical Fluid Extraction*, Butterworths, Stoneham, Mass. (1986). $CO_2$ is readily available, inexpensive, relatively non-toxic, non-flammable, and exhibits a critical temperature of only 31° C. Carbon dioxide is also one of the few organic solvents which occurs naturally in large quantities. Moreover, because $CO_2$ is a gas under ambient conditions, reduction of liquid or supercritical $CO_2$-based solutions to atmospheric pressure induces essentially complete precipitation of solute, thereby facilitating solute/solvent separation.

Consequently, supercritical $CO_2$ has been tapped as an environmentally-sound, organic solvent in such diverse areas as chromatography, biotechnology, polymerization and extraction of thermally-labile constituents from natural products. McLaren, L., et al., *Science*, 159, 197 (1986); Giddings, J. C., et al., *Science*, 162, 67 (1986); Randolph, T. W. et al., *Science*, 238, 387 (1988); Russell, A. J. and Beckman, E. J., *Appl. Biochem. Biotech.*, 31, 197 (1991); Desimone, J. M., et al., *Science*, 257, 5072 (1992); Hubert, P. and Vitzhum, O. G., *Angew. Chem. Int. Ed.*, 17, 710 (1978).

Notwithstanding carbon dioxide's inherent advantages, however, carbon dioxide is a relatively non-polar material and thus will not solubilize highly polar, hydrophilic, or metallic solutes to a significant degree. The most commonly applied strategy for overcoming the poor solubility of polar solutes in $CO_2$ is addition of a co-solvent (also known as a modifier or entrainer), such as a low molecular weight alcohol. Kim, S. and Johnston, K. P., *AIChE J.*, 33, 1603 (1987). The primary disadvantage of this strategy, however, lies in the need to include a large fraction of alcohol to solvate small amounts of solute. Moreover, even addition of alcohol co-solvents will not solubilize significant quantities (mole fractions greater than $10^{-3}$) of hydrophilic solutes such as metals or proteins.

In the late 1980's, researchers at the University of Texas and Battelle's Pacific Northwest Laboratories investigated the use of commercial surfactants and chelating agents to improve the solubility of polar solutes in non-polar supercritical fluids ("SCF's"). Lemert, R. M.; et al., *J. Phys. Chem.*, 94, 6021 (1990); Fulton, J. L. and Smith, R. D., *J. Phys. Chem.*, 92, 2903 (1988). In that regard, studies show that formation of reverse micelles in supercritical alkanes dramatically increases the SCF solubility of amino acids, water-soluble polymers, proteins, and metal-containing compounds. Beckman, E. J., et al. *Supercritical Fluid Technology*, Bruno, T. J. and Ely, J. F., Eds., CRC Press, Chapter 12 (1991); Johnston, K. P., et al., *Supercritical Fluid Science and Technology*, Johnston, K. P. and Penninger, J. M. L., Eds., ACS Symp. Ser. No. 406 (1989).

However, extension of the use of surfactants/chelating agents to environmentally-benign $CO_2$ has been blocked by the experimental observation that commercially available ionic amphophiles, while highly soluble in alkanes such as ethane and propane, exhibit poor to negligible solubility in carbon dioxide at moderate pressures (i.e., 10–500 bar). Consani, K. A. and Smith, R. D., *J. Supercrit. Fl.*, 3, 51 (1990). Conventional chelating agents have shown identical trends. Tingey, J. M. et al., *J. Phys. Chem.*, 93, 2140 (1989).

In an attempt to overcome this problem, one study evaluated improvements of the solubility of diethyl thiocarbamate-metal chelates upon replacement of the alkyl groups thereof with fluoroalkyl moieties. Laintz, K. E., et al., *J. Supercrit. Fl*, 4, 194 (1991). Although this strategy led to a two to three order of magnitude increase in solubility (at 50° C., 1500 psi), the greatest absolute solubility (approximately $4.6 \times 10^{-4}$ gm/gm $CO_2$) achieved is too low to act as the basis for a large-scale extraction process.

At present, the poor solubility of conventional chelating agents in $CO_2$ has prevented process extraction of metals using such chelating agents in $CO_2$. Because of the advantageous properties of $CO_2$ described above, however, it is very desirable to develop a method and chelating agents suitable for performing such extractions.

SUMMARY OF THE INVENTION

Accordingly, the present invention provides a chelating agent suitable for chelating a metal in liquid or supercritical carbon dioxide. The chelating agent comprises a chelating group suitable to chelate the metal and a $CO_2$-soluble functional group covalently attached to the chelating group. The functional group is selected to achieve a chelating agent solubility of at least approximately $10^{-3}$ gram/gram $CO_2$. Preferably, the functional group is selected to achieve a chelating agent solubility of approximately $10^{-2}$ gram/gram $CO_2$. The chelating group preferably comprises an polyiminocarboxylic group (such as an iminodiacetic group), a thiocarbamate group, a dithiocarbamate group, a dithiol group, a thiol group, a picolyl amine group, a bis(picolyl amine) group or a phosphate group. The chelating group is preferably selected from a group consisting of a dithiocarbamate group, a thiol group and a picolyl amine group.

To achieve the desired solubility, the $CO_2$-soluble functional group preferably comprises a fluorinated polyether group, a silicone group, a fluorinated polyalkyl group, a phosphazene group or a fluorinated polyacrylate group. More preferably, the $CO_2$-soluble functional group comprises a fluorinated polyether group, a silicone group or a fluorinated polyalkyl group. Most preferably, the $CO_2$-soluble functional group comprises a fluorinated polyether group, such as poly(hexafluoropropylene oxide) group or a fluoralkyl group such as a perfluorohexyl group.

The present invention also provides a method of extracting a metal from a matrix containing the metal and at least one other material, comprising the steps of: (a) dissolving in a vessel a chelating agent suitable for forming a coordinated complex with the metal in carbon dioxide, the chelating agent comprising a chelating group as described above; and (b) contacting the dissolved chelating agent with the matrix in the vessel. As set forth above, a solubility of at least approximately $10^{-2}$ gram/gram $CO_2$ is preferably achieved.

After contacting the dissolved chelating agent with the matrix for a predetermined period of time, the pressure in the vessel is reduced to precipitate the chelating agent and the coordinated metal. Preferably, the pressure is reduced to atmospheric pressure.

The $CO_2$-soluble chelating agents of the present invention are prepared using a design strategy whereby conventional polar/ionic chelating moieties are derivatized with relatively highly $CO_2$-soluble ("$CO_2$-philic") functional groups. The solubilities of the target molecules in carbon dioxide are several (e.g., three to four) orders of magnitude greater than conventional amphophiles at moderate temperatures and moderate pressures.

The temperature at which the preferred solubility of $10^{-2}$ gm/gm $CO_2$ is achieved is preferably in the range of approximately 0° to 100° C. More preferably the temperature is in the range of approximately 20° to 50° C. Preferably, the pressure at which such solubility is achieved is in the range of approximately 500 to 5000 psi. More preferably, the pressure is in the range of approximately 900 to 3000.

The present compounds extend the application of environmentally-benign, yet nonpolar, $CO_2$ to separation processes previously inaccessible, such as heavy metal extraction from contaminated soil or water. Indeed, extension of the present $CO_2$-philic derivatization scheme to extremely hydrophilic materials such as iminodiacetic acid and thiocarbamate-functional chelates fully demonstrates the usefulness of $CO_2$-philic groups in chelate design.

Moreover, the present invention provides several unique advantages in the extraction of metals from complex matrices such as soil. First, the use of carbon dioxide allows ready extraction (in part, because of the low viscosity of either liquid or supercritical carbon dioxide) followed by ready concentration by depressurization. The ease of concentration allows both recycle of the chelating agent and the carbon dioxide solvent. Second, generation of chelating agents which incorporate $CO_2$-philic functional groups improves the solubility of chelating agents in carbon dioxide by several (three to four) orders of magnitude, thus bringing chelation in supercritical carbon dioxide from the analytical realm to the process realm. Third, use of silicone, fluoroether and fluroalkyl $CO_2$-philic groups provides flexibility in the design of target molecules in that such molecule systems can be optimized in terms of required process pressure versus cost of the target molecule system.

BRIEF DESCRIPTION OF THE DRAWINGS

FIG. 1(*b*) illustrates a general structure of a fluoroalkyl functional group suitable for functionalizing chelating head groups.

FIG. 1(*c*) illustrates a general structure of a silicone functional group suitable for functionalizing chelating head groups.

FIG. 1(*d*) illustrates a general structure of a fluorinated polyacrylate functional group suitable for functionalizing chelating head groups.

FIG. 1(*e*) illustrates a general structure of a phosphazene functional group suitable for functionalizing chelating head groups.

FIG. 1(*f*) illustrates a number of preferred structures for chelating agents designed to extract certain metals.

FIG. 1(*g*) illustrates schematically the structure of a chelating agent incorporating a spacer group for minimizing adverse effects of a strong electron withdrawing $CO_2$-philic group upon the chelating head group.

FIG. 2(*b*) illustrates a general structure of fluoroether-functional chelating agents prepared using a hexafluoropropylene oxide precursor.

FIG. 2(*c*) illustrates schematically a synthetic scheme for production of fluoroalkyl- and fluoroether-functionalized chelating agents comprising a purine group or a thio-functional purine group.

FIG. 2(*d*) illustrates schematically a synthetic scheme for production of fluoroalkyl- and fluoroether-functionalized chelating agents comprising a phosphate ester group.

FIG. 2(*e*) illustrates schematically a synthetic scheme for production of fluoroalkyl- and fluoroether-functionalized chelating agents comprising an iminodiacetic acid group.

FIG. 5(*c*) illustrates the solubility of two silicone-functionalized chelating agents at 40° C.

DETAILED DESCRIPTION OF THE INVENTION

Figure 1A:
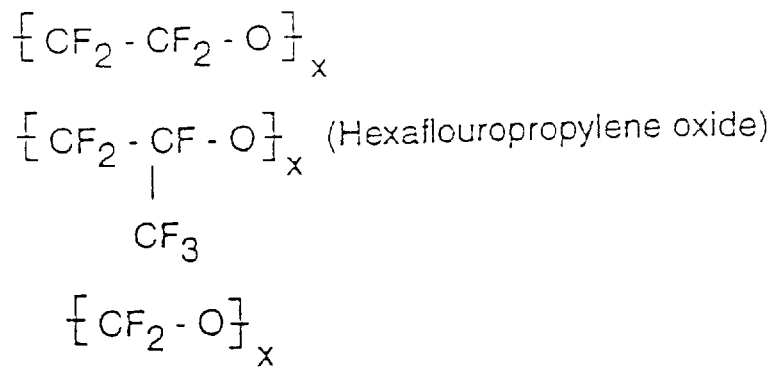
FIG. 1(*a*) illustrates a general structure of a number of fluoroether functional groups suitable for functionalizing chelating head groups.
Figure 1B:
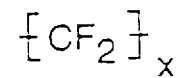

Commercially-available chelating agents exhibit poor solubility in $CO_2$. It has been discovered, however, that such chelating agents can be "redesigned" for use in $CO_2$. Consequently, to extend the use of $CO_2$ in separation processes to hydrophilic/metallic solutes, novel $CO_2$-soluble chelating agents have been designed and synthesized.

Identification of Chelating Functional Groups

A chelate is a coordination compound in which an ion of metallic elements such as, for example, U, Pb, Hg, As, Au, Ni, Co and Cu is attached by coordinate links to generally two or more nonmetal atoms in the same molecule. In general, the coordinating atoms are electron donating atoms of the elements O, S, and N. Thus, numerous compounds comprising atoms of O, S and/or N act as chelating agents. See e.g., *Analyst*, 116 (1991) and Calmon, C. and Gold, H., *Ion Exchange for Pollution Control*, Water Pollution Control Technology Series, the disclosures of which are incorporated herein by reference. Although the types of compounds capable of forming coordinate complexes with metal ions are too numerous to categorize beyond the generalization that such compounds comprise O, S, and/or N, examples include compounds comprising thio groups, dithio groups, thiol groups, dithiol groups, amine groups, hydroxyl groups, carboxilic groups and/or carbamate groups. Specific examples of chelating agent groups suitable for attachment to the present $CO_2$-philic functional groups include polyaminocarboxylic acid groups (e.g., an iminodiacetic group), thiocarbamate groups, dithiocarbamate groups dithiol groups, thiol groups, picolyl amine groups, bis(picolyl amine) groups, and phosphate groups.

Identification of $CO_2$-philic Functional Groups

Like their conventional analogs, the present molecules possess polar head groups designed to accomplish chelation. Unlike conventional compounds of this nature, in which an alkane tail (or tails) is covalently bonded to the head group, however, the present target molecules possess a hydrophobic tail comprising a functional group designed to interact favorably, in a thermodynamic sense, with carbon dioxide. Such functional groups may be referred to as "$CO_2$-philic" groups.

Whereas numerous reports suggest that the solvent power of carbon dioxide is similar to that of hexane, it has now been discovered that these suggestions are incorrect. Design of $CO_2$-philic functional groups must incorporate knowledge of the molecular properties of carbon dioxide. In fact, it has been discovered that many of the most $CO_2$-philic functional groups available are almost entirely insoluble in alkanes.

Although the solubility parameter (a measure of bulk solvent properties) of supercritical carbon dioxide approaches that of hexane above 300 bar at 40° C., specific interactions involving $CO_2$ and those involving hexane will differ greatly at the molecular level. Unlike hexane, $CO_2$ is a Lewis acid and possesses a quadruple moment. Indeed, studies of molecular level solvent properties of $CO_2$ have been more closely likened to the behavior of ethyl acetate, or perhaps even acetone, rather than hexane. Walsh, J. M. et al., *Fluid Phase Equil.*, 33, 295 (1987); Nyatt, J. A., *J. Org. Chem*, 49, 5097 (1984).

Whereas fluoroether and silicone polymers exhibit high solubilities in $CO_2$ at moderate pressures, polyolefin waxes of comparable molecular weight exhibit solubilities which are several orders of magnitude lower at the pressures examined. These results would not be expected if the solvent power of $CO_2$ were simply "like that of hexane". Furthermore, fluoroethers are generally immiscible with pentane or hexane, compounds which have been promoted as potential screening agents for $CO_2$-solubility.

Given the known physical properties of $CO_2$, and extensive literature data on supercritical $CO_2$/solute phase behavior (see e.g., Dandge, D. K et al., IEC Prod. *Res. Dev.*, 24, 162 (1985); Francis, A. W., *J. Phys. Chem.*, 58, 1099 (1954); U.S. Pat. No. 4,913,235; and Iezzi, A., *Fluid Phase Equil*, 52, 307 (1989)), it has been determined that inclusion of the particular functional groups of Table 1 in a solute molecule will contribute to relatively high solubility in $CO_2$.

TABLE 1

| Functional Groups Which Interact Favorably With Carbon Dioxide | |
|---|---|
| Functional Groups | Properties Leading to Favorable Interaction |
| Fluorinated Polyethers (e.g., Hexafluoropropylene Oxide) | Low solubility parameter, (4–6 $(cal/cm^3)^{0.5}$), electron-donating capability |
| Silicones (e.g., Dimethyl Siloxane) | Low solubility parameter (7–9 $(cal/cm^3)^{0.5}$) |
| Fluoroalkyls | Low solubility parameter (6–7 $(cal/cm^3)^{0.5}$), low dipolarity polarizability parameter, (−0.5–0.0) |
| Fluorinated polyacrylates | Low solubility parameter, electron-donating capability |
| Poly(phosphazenes) | Electron-donating capability |

Figure 1C:
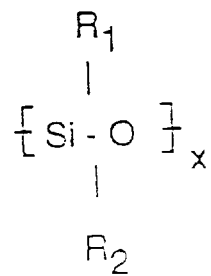
Figure 1D:
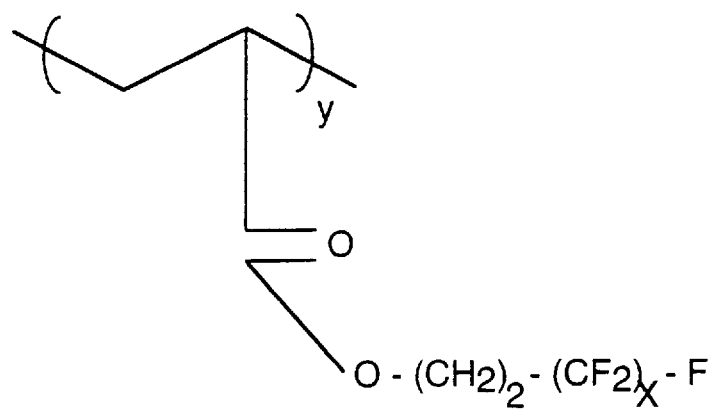
Figure 1E:
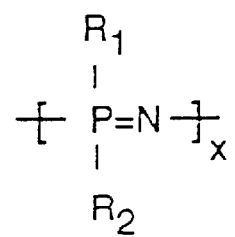

The $CO_2$-philic groups of Table 1 are illustrated schematically in FIGS. 1(a)–1(e). In FIGS. 1(c) and 1(e), $R_1$ and $R_2$ can, in general, be any alkyl, aromatic or alkyl-aromatic group. Preferably $R_1$ and/or $R_2$ comprise a fluorinated alkyl group.

Previous studies with fluoroalkyl sulfonate surfactants show that solubility in carbon dioxide rises significantly upon replacement of —$CH_2$— with —$CF_2$— in such compounds. Hoefling, T. A., et al., *J. Phys. Chem.*, supra, the disclosure of which is incorporated herein by reference. These studies (performed with fluoroalkyl-functional, twin-tailed sulfonates) showed that a fluoroalkyl chain length of $C_5$ or $C_6$ and greater is required to generate 1–5 weight % solubility of sulfonates in $CO_2$. It is believed that fluoroalkyls will exhibit similar $CO_2$-philic behavior in solubilizing metal chelating groups in $CO_2$.

Another study recently showed that fluorinated polyacrylates are extremely soluble in carbon dioxide. Desimone, J. M., et al., *Science*, 257, 5072 (1992), the disclosure of which is incorporated herein by reference. This study demonstrated orders-of-magnitude improvement in $CO_2$-solubility of high molecular weight polymers of fluoroacrylates compared to their alkyl analogs. It is, therefore, believed that fluorinated polyacrylates will also be suitable for use in the present invention.

Previously, solubilities in $CO_2$ of chelating agents greater than approximately $4.6 \times 10^{-4}$ have been unattainable. Under the present invention, however, solubilities greater than $10^{-3}$ are readily attainable. To enable viable process extraction, however, a solubility of at least $10^{-2}$ gm chelating agent/gm $CO_2$ is preferably attained. In this regard, fluoroether, fluoroalkyl and silicone derivatization has been found to increase the solubility of conventional chelating agents by three to four orders of magnitude, resulting in absolute solubilities in the range of approximately $10^{-2}$ to $10^{-1}$ gm/gm $CO_2$ (i.e., 1 to 10 wt %).

Of the functional groups of Table 1, fluoroether compounds exhibit the highest $CO_2$-solubility. Fluoroalkyl compounds exhibit the next highest $CO_2$-solubility. Thus, fluoroether-derivatized chelating agents generally exhibit higher solubilities than chelating agents derivatized with other functional groups previously studied at a given temperature and pressure. Tables 2 and 3 provide solubility data for a fluoroether-functionalized dithiol chelating agent and a fluoroether-functionalized picolyl amine chelating agent, respectively. As seen, solubilities in the range of approximately 2.10 to 4.40 wt % were attained.

TABLE 2

Fluoroether derivatized dithiol

| $CO_2$ | Wt. % | Cloud Point |
|---|---|---|
| 19.5 | 4.41 | 940 |
| 23.2 | 3.71 | 970 |
| 27.5 | 3.13 | 980 |
| 31.9 | 2.70 | 1000 |
| 36.1 | 2.38 | 1020 |
| 40.4 | 2.13 | 1040 |

TABLE 3

Fluoroether derivatized picolyl amine

| $CO_2$ | Wt. % | Cloud Point |
|---|---|---|
| 25.3 | 4.34 | 1000 |
| 29.3 | 3.75 | 1023 |
| 33.3 | 3.30 | 1080 |
| 37.3 | 2.94 | 1025 |

In general, the solubility of derivatized chelating agents can be increased by raising the pressure. However, the pressure is preferably in the range of approximately 500 to 5000 psi and, more preferably, in the range of approximately 900 to 3000 psi. The temperature is preferably in the range of approximately 0° to 100° C. and, more preferably, in the range of approximately 20° to 50° C.

To ensure adequate solubility is achieved, at least three repeat units of a fluoroether such as hexafluoropropylene oxide (resulting in a molecular weight of approximately 500) are attached to a chelating group. In the case of a silicone functional group, at least six repeat units are preferably attached (resulting in a molecular weight of approximately 500). In the case of a fluoroalkyl functional group, at least six repeat units are preferably attached, resulting in a molecular weight of 300). In the case of a fluorinated polyacrylate functional group, at least three repeat groups are preferably attached (resulting in a molecular weight of approximately 1200). In the case of a phosphazene functional group, at least six repeat units are preferably attached.

Several chelating head groups for use in the present invention were chosen as a result of previous studies showing their efficacy in coordinating one or more metals. In that regard, FIG. 1(f) illustrates a number of such chelating head groups, corresponding to preferred $CO_2$-philic functional groups and the metal the resultant target molecules are designed to extract.

In general, non-ionic chelating head groups have been found to work well with all the $CO_2$-philic functional groups of Table 1 studied. Preferably, ionic chelating head groups (which are particularly insoluble in $CO_2$) are functionalized with strongly $CO_2$-philic functional groups such as fluoroethers to achieve suitable solubility at moderate temperatures and pressure fluoroethers.

Figure 1G:
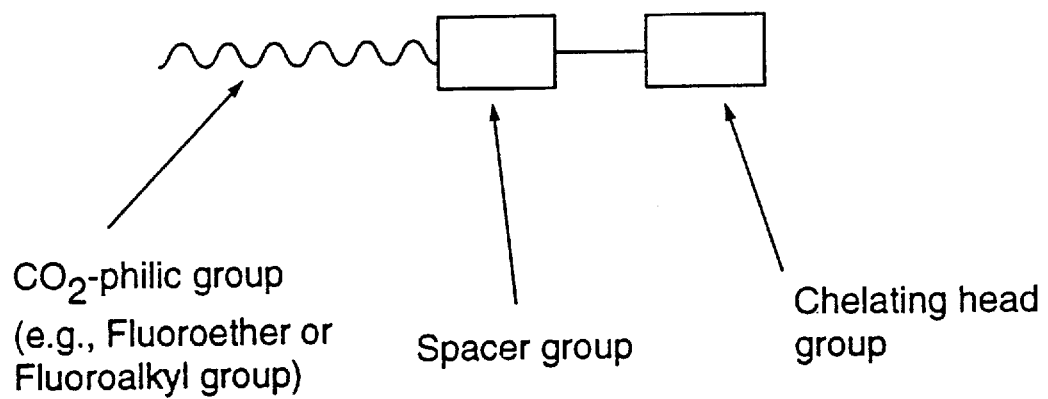

Further, fluoroethers and fluoroalkyls are strong electron withdrawing agents, a property adversely affecting chelation. Therefore, in some cases when fluoroethers and fluoroalkyls are used as a $CO_2$-philic functional group, a non-electron withdrawing spacer group is preferably inserted between the fluoroether or the fluoroalkyl and the chelating head group (see FIG. 1(g)) to minimize the detrimental effect of the electron withdrawing group. Preferably the spacer group is a $(CH_2)_x$, group wherein preferably $x \geq 3$.

Synthesis of Fluoroalkyl- and Fluoroether-functional Chelating Agents

Figure 2A:
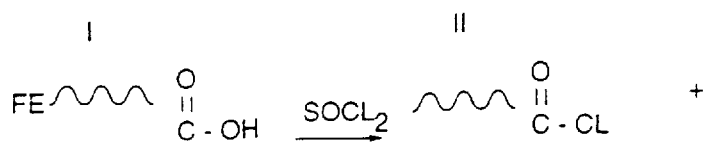
FIG. 2(*a*) illustrates schematically a synthetic scheme for production of fluoroalkyl- and fluoroether-functionalized chelating agents.
Figure 2A:
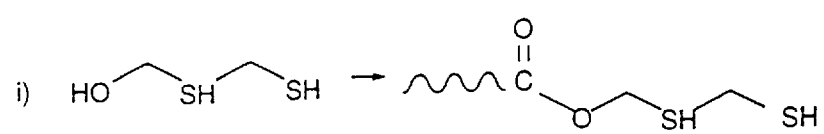
Figure 2A:
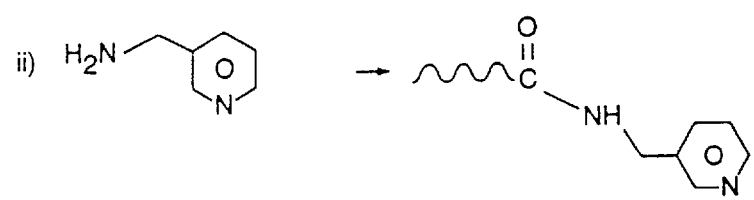
Figure 2A:
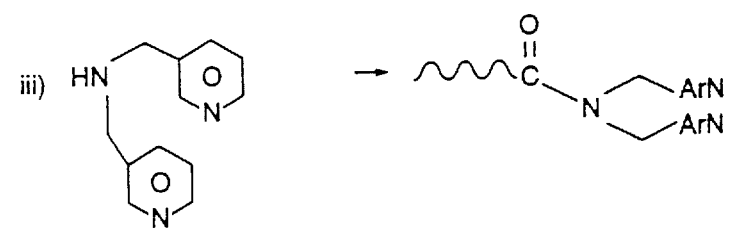
Figure 2A:
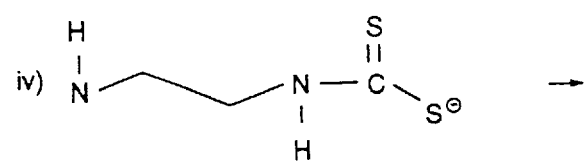
Figure 2A:
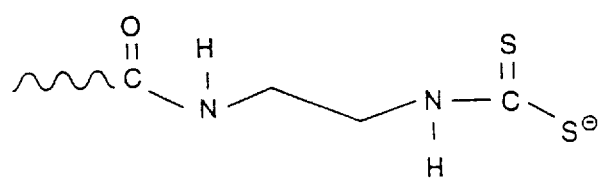

A general synthetic scheme to prepare the fluoroether-functionalized chelating agents of the present invention is illustrated schematically in FIG. 2(a). The synthetic strategy was developed in an attempt to employ chemical routes which are both as convergent as possible and as high yield as possible.

Figure 2B:
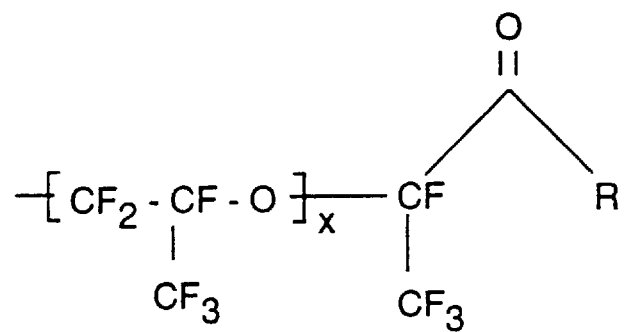

Generally, to synthesize the $CO_2$-soluble chelating agents, an acyl chloride meta-precursor(II) was first prepared from the acid-functional fluoroether (I) via reaction with thionyl chloride ($SOCl_2$). The acid chloride was then used to prepare each of the target molecules by reaction with a hydroxy- or amino- functionalized chelating head group (see i-iv of FIG. 2(a)). The general structure for resultant hexafluoropropylene oxide functionalized chelating agents is shown schematically in FIG. 2(b), in which R represents the chelating head group. In the case of a hexafluoropropylene oxide having a molecular weight of approximately 2500, the value of x in FIG. 2(b) is 14.

Fluoralkyl-functionalized chelating agents may be synthesized via a similar scheme to that shown in FIG. 2(a). In general, an acyl chloride precursor may be prepared from an acid-functionalized fluoroalkyl. The acyl chloride is then used to prepare the target molecules as set forth above. One may alternatively obtain commercially available acyl-chloride-functionalized fluoroether and fluoralkyl for use in synthesis of the present chelating agents.

EXAMPLES

Oligomers of hexafluoropropylene oxide, capped (mono) with a carboxylic acid group, were received from DuPont (Krytox functional oils of approximately 2500, 5000, and 7500 molecular weights). In that regard, an approximately 2500 molecular weight, mono-carboxy terminated oligomer of hexafluoropropylene oxide (Krytox 157FSL, DuPont) was transformed to the acyl chloride using thionyl chloride. In a typical experiment, 10 g of Krytox 157FSL was dissolved in 50 ml of a mixture of $C_2Cl_4F_2/C_2Cl_3F_3$ or, preferably, in perfluoromethyl cyclohexane; to which was added thionyl chloride and dimethyl formamide (Aldrich), each in approximately 100% molar excess (e.g. 0.95 gram of thionyl chloride (8 mmole) and 0.58 grams (8 mmole) of dimethyl formamide) in a reaction flask equipped with a dry-ice condenser. The temperature was raised to approximately 80° C., and the mixture stirred for several hours (approximately six hours) under an inert atmosphere. Following removal of excess solvent and residual reactant under vacuum the product was analyzed for acyl chloride (FT-IR, carbonyl peak shifts from 1776 to 1809 $cm^{-1}$, $^1H$ NMR, disappearance of COOH proton at 9.63 ppm, $^{13}C$ NMR, shift of carbonyl carbon peak from 161 to 163 ppm). The acyl chloride was then used to prepare each of the target molecules.

a. Synthesis of picolyl amine, bis(picolylamine) and dithiol chelates.

Chelating agents containing dithiol (i in FIG. 2(a)), picolyl amine (ii in FIG. 2(a)) and bis(picolyl amine) (iii in FIG.

2(a)) functional groups have been prepared. In a typical experiment, 10 grams of fluoroether acyl chloride (I) (4 mmole) were dissolved in 50 cm$^3$ dry $C_2Cl_3F_3$ (freon 113). Subsequently, 0.58 grams picolyl amine (6 mmole, Aldrich) in 10 cm$^3$ dry THF were added, as well as an amount of a crosslinked, aminopyridine-functional resin (PolyDmap, Reilly Industries) to scavenge HCl. After stirring for several hours, the PolyDmap was removed by filtration, the solvent removed under vacuum, and the product was washed several times with ether. Characterization of the product showed the formation of the amide (FT-IR, 1720 cm$^{-1}$).

Chelating agents comprising bis(picolyl amine) and dithiol groups were prepared analogously from bis(picolyl amine) and 2, 3 dithio-1-propanol (Aldrich), respectively.

b. Synthesis of thiocarbamate-functionalize chelating agents.

For a chelating agent comprising thiocarbamate (iv of FIG. 2(a)), the chelating head group was prepared as follows: N,N' dimethyl ethylene diamine was dissolved in dry ether at –70° C., after which butyl lithium (1 molar solution in ether) was added dropwise to a 1:1 molar ratio with the diamine. After approximately one hour, carbon disulfide (1:1 molar ratio to diamine) was added with stirring while raising the temperature slowly to 0° C. The product was recovered from the solvent conventionally, and was then dissolved in DMSO, and added to a solution of acyl chloride precursor (I) in a dioxane/freon 113 mixture, with a crosslinked HCl scavenger resin present. The product was subsequently recovered from the solvent conventionally.

c. Synthesis of purine and thio-functional purine chelates.

Figure 2C:
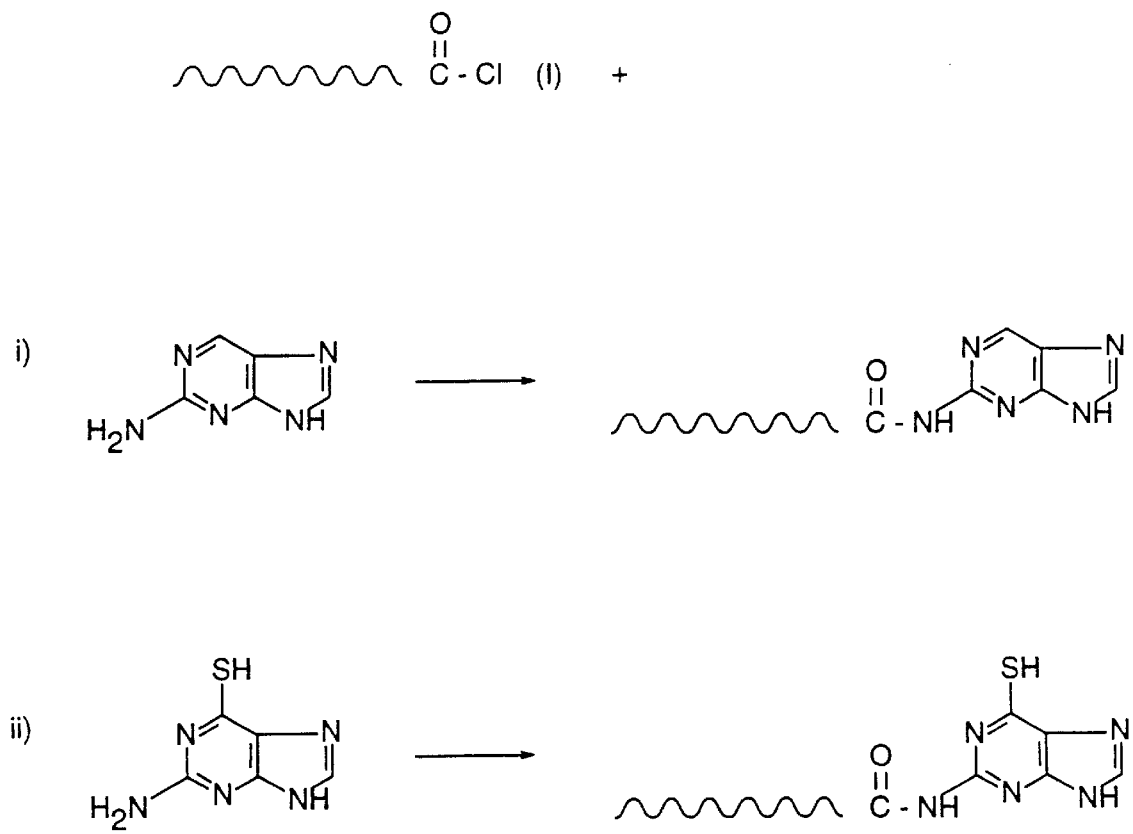

In the case of purine (i of FIG. 2(c)) and thio-functional purine (ii of FIG. 2(c)), the chelating head group compounds were dissolved in DMSO, then added to a solution of fluoroether acyl chloride precursor (I) and PolyDmap in a $C_2Cl_3F_3$/Dioxane mixture.

d. Synthesis of phosphate ester chelates.

Figure 2D:
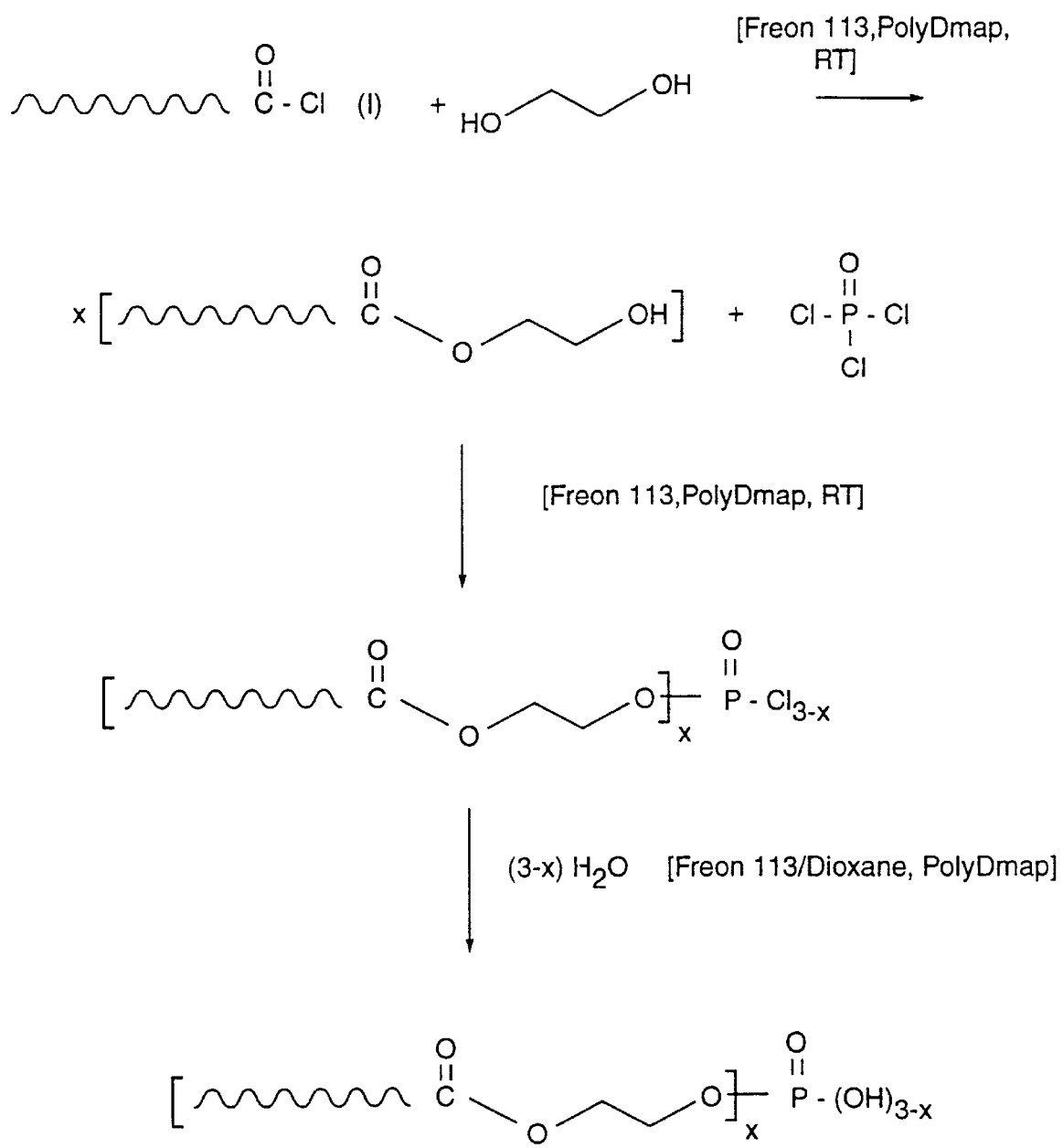

A phosphate ester chelating agent (see FIG. 2(d)) was prepared by reaction of acyl chloride (I) with a large molar excess of ethylene glycol (at room temperature (RT), in previously dried freon 113 and in the presence of an HCl scavenger such as PolyDmap) to generate a hydroxy functional product. The hydroxy functional product was reacted with phosphorous oxychloride (in Freon 113, at room temperature and in the presence of an HCl scavenger) in an appropriate ratio to generate single, twin or triple tailed materials as desired. Excess water was added to the product to hydrolize the remaining P—Cl bond.

e. Synthesis of aminodiacetic acid chelates.

Figure 2E:
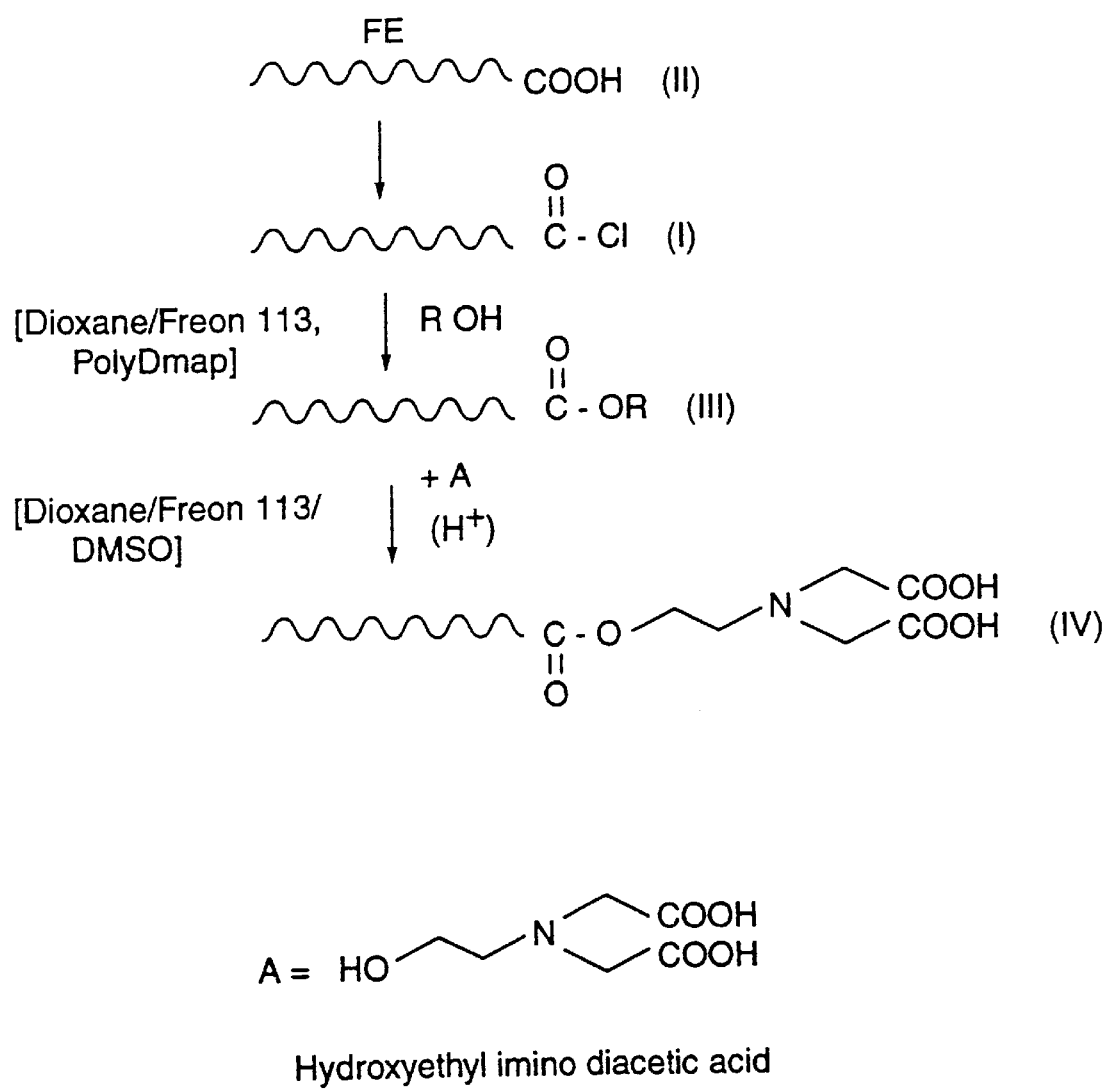

Because iminodiacetic acid is soluble only in water, the reaction scheme is somewhat different than those described above and is set forth schematically in FIG. 2(e). An iminodiacetic acid ("IDA") functional material is prepared by reaction of acyl chloride precursor (I) with, for example, nitrophenol or N-hydroxy succinimide to form an activated ester (III). This reaction takes place at room temperature in an appropriate solvent (such as a Dioxane/Freon 113 mixture) and in the presence of an HCl scavenger such as PolyDmap. Activated ester (III) is reacted with hydroxyethyl imino diacetic acid (A) with a small amount of acid catalyst in an appropriate solvent (such a Dioxane/Freon 113 mixture) at approximately 50° to 70° C. to give product (IV).

Synthesis of silicone-functional chelating agents

Figure 3:
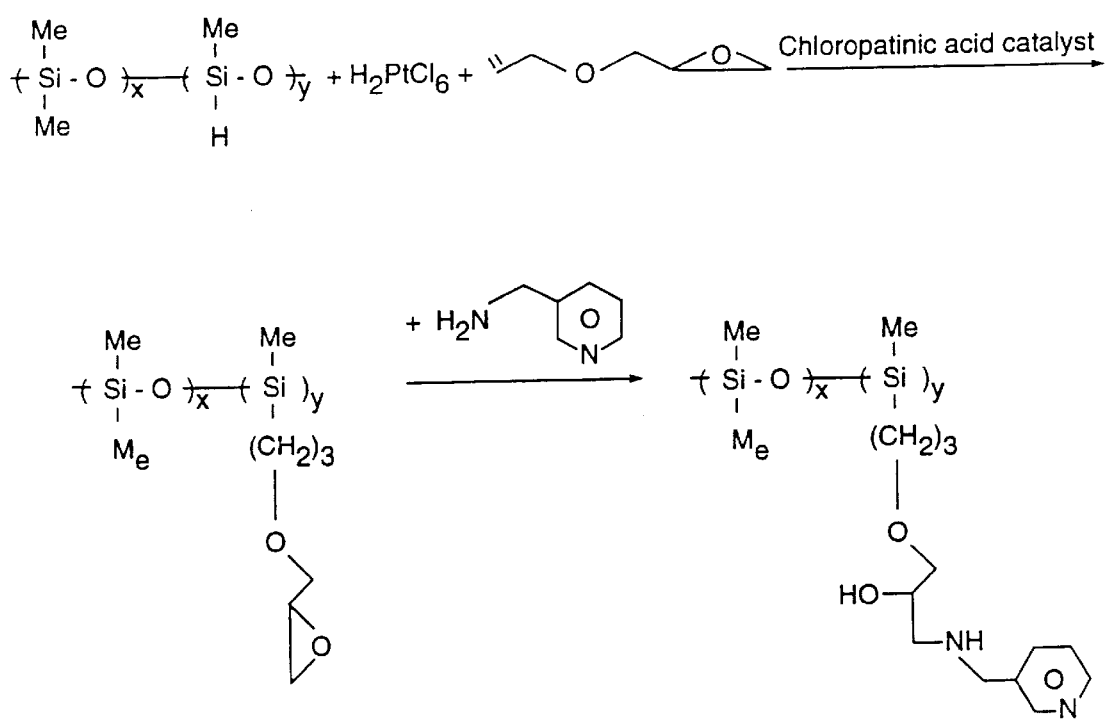
FIG. 3 illustrates schematically a synthetic scheme for production of silicone-functionalized chelating agents.

A synthetic scheme for preparation of silicone-functional chelating agents is shown in FIG. 3. Linear, monofunctional molecules as well as branched multi-functional molecules were evaluated. Branched molecules were synthesized via functionalization of a hydromethyl/dimethyl siloxane copolymer (Huls-Petrarch PS123.5) with allyl glycidal ether (AGE, Aldrich).

Using $^{29}$Si NMR, the PS123.5 precursor was ascertained to possess the structure $(DMS)_{24}(HMS)_6$ (where DMS refers to dimethyl siloxane and HMS to hydromethyl siloxane), providing six reactive sites per molecule. During the synthesis of the silicone-functionalized chelating agents, each HMS residue was functionalized either with AGE, or with a silicone "blocking agent", allyl tris(trimethylsiloxy) silane (ATSS; Huls-Petrarch).

In a typical experiment, 10 g of PS123.5 is dissolved in 100 cm$^3$ of dry toluene in a 250 cm$^3$ three neck round bottom flask; varying amounts of AGE are then added, depending on the ultimate number of chelating head groups desired (1 to 6). Next, 30 ^gK^Rl of a 0.1M chloroplatinic acid (Aldrich) solution in isopropanol is added, and the mixture refluxed for 6 hr. Next, the appropriate amount of ATSS is added to block the remaining hydromethyl groups, an additional 30 ^gK^Rl of the catalyst is injected, and the mixture is refluxed overnight. Following removal of the solvent, residual AGE, and ATSS under vacuum, the product is characterized using FT-IR (disappearance of the strong Si-H signal at 2150 cm$^{-1}$) and $^1$H NMR (integrity of the oxirane group).

a. Synthesis of silicone-functional picolylamine and bis (picolyl amine) chelates.

Following confirmation of production of the AGE-functional silicone, the pendant oxirane groups are reacted with amino- or hydroxyl-functional chelating head groups. For example, the AGE-functional silicone was reacted with a large molar excess of picolyl amine or bis(picolyl amine) in an appropriate solvent (e.g., chloroform) and reflux at 50° to 70° C. for several hours, followed by solvent removal under vacum.

The procedure for synthesis of the linear silicone-functional chelating agents is analogous to that described above, except that a HMS-DMS-DMS-HMS precursor (Huls-Petrarch 09814) is employed. One end functionalized with AGE, the other with the ATSS blocking agent. The pendant oxirane is then reacted with an amino- or hydroxyl-functional chelating head group as described above.

Characterization

Solubility in Carbon Dioxide

Figure 4:
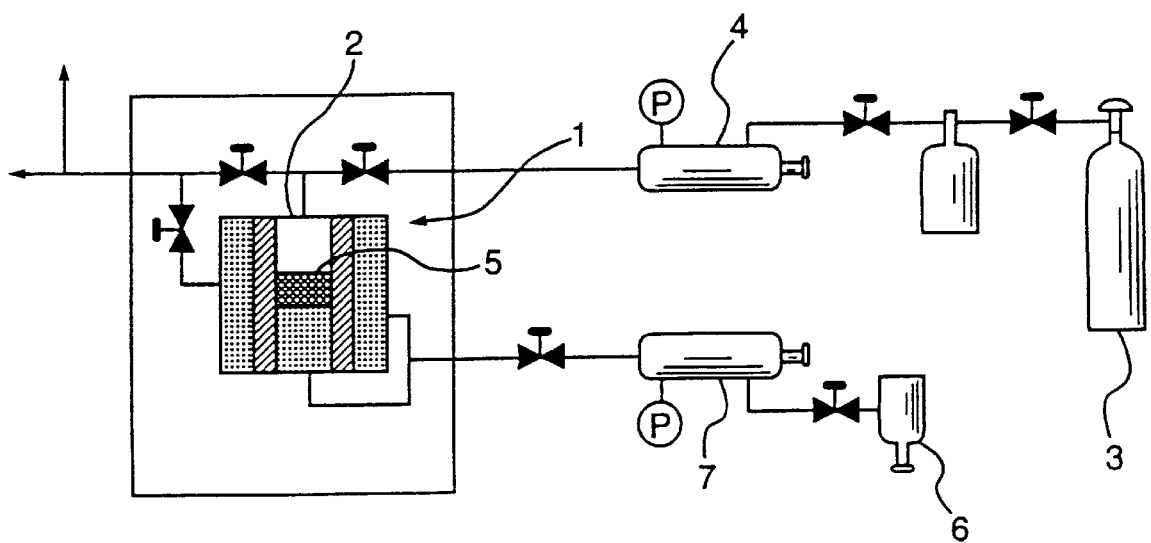
FIG. 4 is a schematic illustration of an apparatus for performing solubility studies.

Phase behavior of the chelating agents in carbon dioxide (Bone dry grade) was performed using a high pressure, variable volume view cell 1 (D. B. Robinson and Assoc.), shown in FIG. 4. Typically, a known amount of chelating agent is added to the top of the quartz tube sample cell 2, as well as a number of steel ball bearings (to provide mixing). The tube is then sealed inside the steel housing, and a known volume of carbon dioxide (from cylinder 3) at its vapor pressure is injected via a compressor using a Ruska syringe pump 4. Quartz sample tube 2 contains a floating piston 5 which separates the sample from the pressure-transmitting fluid, in this case silicone oil from reservoir 6. The pressure on the sample is raised (via movement of the piston due to injection of silicone oil by a second Ruska pump 7) to a point where a single phase is present (mixing is accomplished via motion of the ball bearings (not shown) upon rocking of the entire cell). The pressure is then lowered via slow withdrawal of silicone oil from beneath the piston until the first signs of turbidity appear. This procedure is repeated until the cloud point is known to within a few psi. The pressure is then lowered to the vapor pressure, additional carbon dioxide is injected, and a new cloud point is measured; eventually an entire cloud point curve is mapped.

Figure 5A:
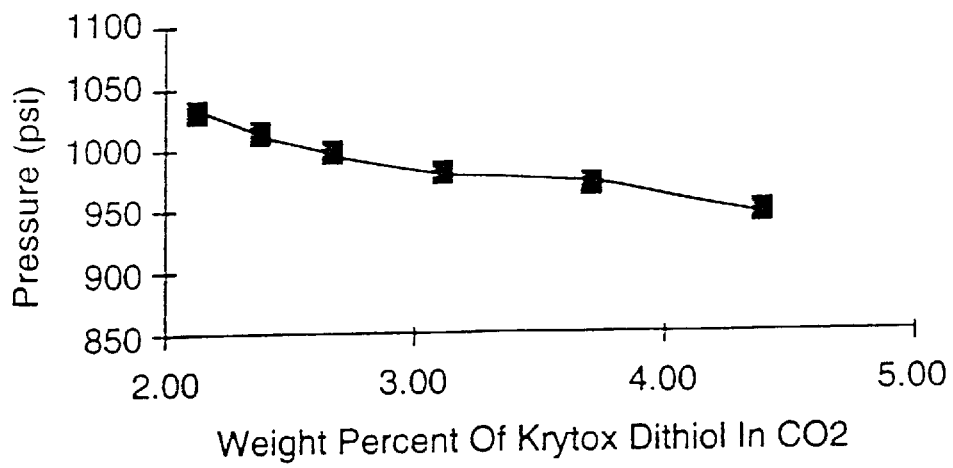
FIGS. 5(*a*) and (*b*) illustrate the solubility of two fluoroether-functionalized (2500 molecular weight poly(hexafluoropropylene oxide) chelating agents in $CO_2$ at 40° C.
Figure 5B:
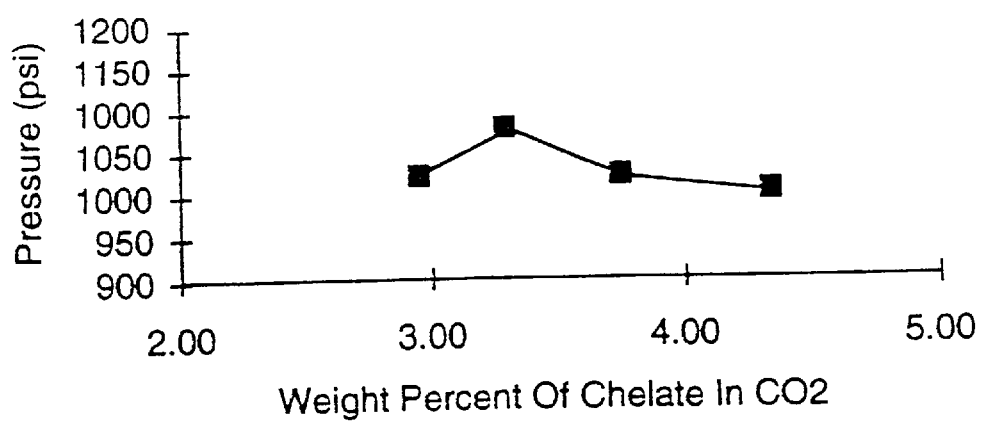
Figure 5C:
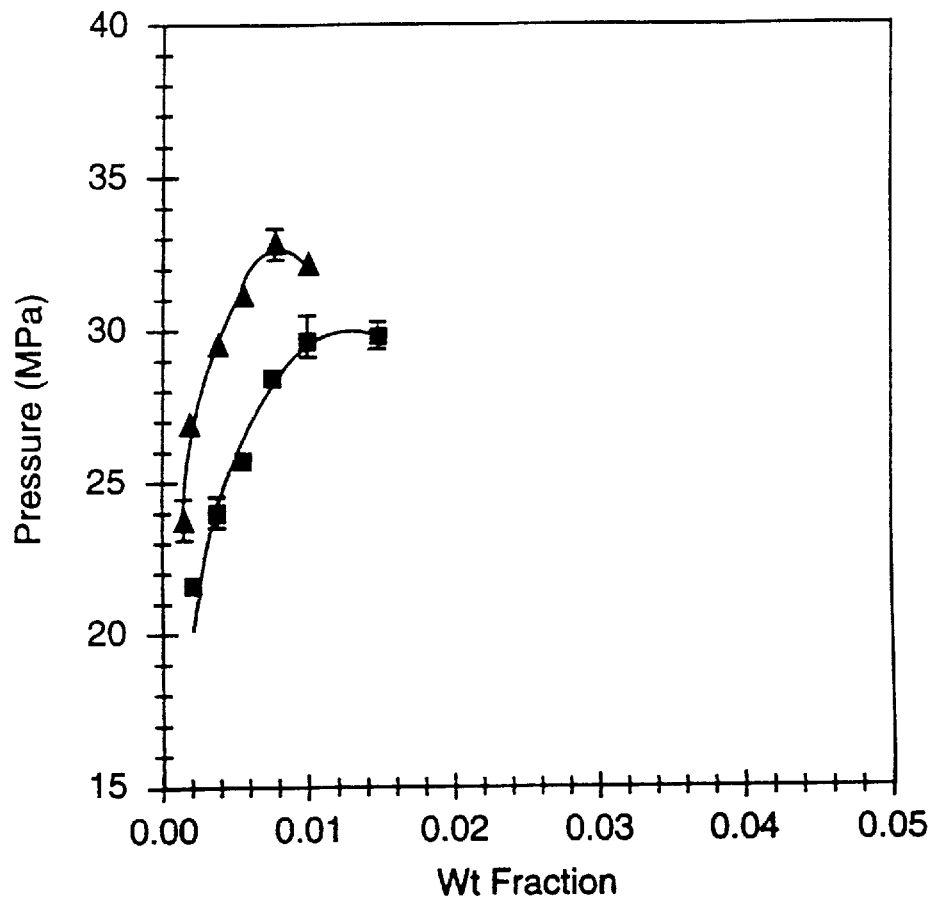

Cloud point curves (FIG. 5(a) and 5(b) for dithiol and picolyl amine, respectively) show that the fluoroether-functional chelating agents are extremely soluble in $CO_2$ at moderate pressures and 40° C. FIG. 5(c) illustrates cloud point curves for a siliconefunctionalized picolyl amine (squares) and bis (picoly/amine) (triangles) at 40° C.

Extraction Studies

In extraction studies, Laboratory sand is spiked with metal according to the following procedure: 50 grams of sand (Fisher) is slurried with 100 $cm^3$ of an aqueous solution of, for example, lead nitrate for several hours. The water is then removed under vacuum while stirring vigorously in the rotary evaporator. Metal loadings of 1 to 3 milliequivalent per 100 grams of sand are thus prepared. A pre-extraction "blank" is then generated by slurrying a sample of the spiked sand with a hot nitric acid solution for several hours, then analyzing the aqueous extractant via atomic absorption spectroscopy (AAS).

Extraction is performed using the chelating agents of the present invention in both freon 113 and $CO_2$ for comparison. In the case of the freon, a solution of chelating agent is slurried with the spiked sand for several hours, after which time the sand is removed by filtration, washed with additional freon, then dried. The sand is then subjected to nitric acid digestion as before, and the aqueous extract analyzed for metal concentration via AAS. In addition, an extraction using pure freon 113 is performed as an additional blank.

In extractions using carbon dioxide, spiked sand plus the chelating agent are added to the extraction vessel (40 $cm^3$, 7500 psi max., constructed at University of Pittsburgh), following which the system is pressurized via an Eldex piston pump. Upon reaching the operating pressure, the Eldex pump is shut off, and carbon dioxide is circulated through the system using the high pressure gear pump (Micropump), while the sand slurry is stirred via a magnetic stir bar (a filter at the vessel outlet prevents entrainment of sand by the $CO_2$). After 30 minutes of recirculation, pure $CO_2$ is pumped through the system by the Eldex pump, exiting at the back pressure regulator (Tescom), where the pressure drops to atmospheric and the solute precipitates and is collected. The system is then depressurized and the sand collected for nitric acid digestion and analysis for residual metal content.

Several experiments, showed that a bis(picolyl amine) functional fluoroether will extract nickel and lead from samples of laboratory sand which had been spiked with a nickel salt and a lead salt, respectively.

Hereinabove there exists a deterioration of the extraction efficiency of some of the chelating agents when functionalized with an electron withdrawing tail such as perfluoropolyether of fluorinated alkyl group as compared to their non-electron withdrawing polydimethyl siloxane counterpart. Hereinbelow further experiments are carried out to study this and other issues.

Further Examples

Unless otherwise specified, all chemicals were received from Aldrich Chemical Company. Perfluoroheptane was received from 3M Chemicals (commercial name: 3M Performance Fluid-5070, research grade), and PolyDMAP, a polymeric agent used for scavenging HCl, was purchased from Reilly Industries, Indianapolis, Ind. Except for the drying of solvents with molecular sieves, no further purification was performed on the raw materials. Analytical characterizations were performed using a Mattson Polaris Fourier Transform Infrared (FT-IR) spectrometer and a Bruker MSL 300 Nuclear Magnetic Resonance (NMR) 300 Mhz spectrometer capable of obtaining both $^1H$ and $^{13}C$ spectra.

The chelating agent thenoyl trifluoroether picolyl amine, fluoroether bis(picolyl amine), fluoroether dithiocarbamate and fluoroether dithiol were synthesized according to the procedure outlined hereinabove. The procedures for the synthesis of the other chelating agents follow.

a. Fluoroalkyl bis(Picolyl Amine)

Figure 6:
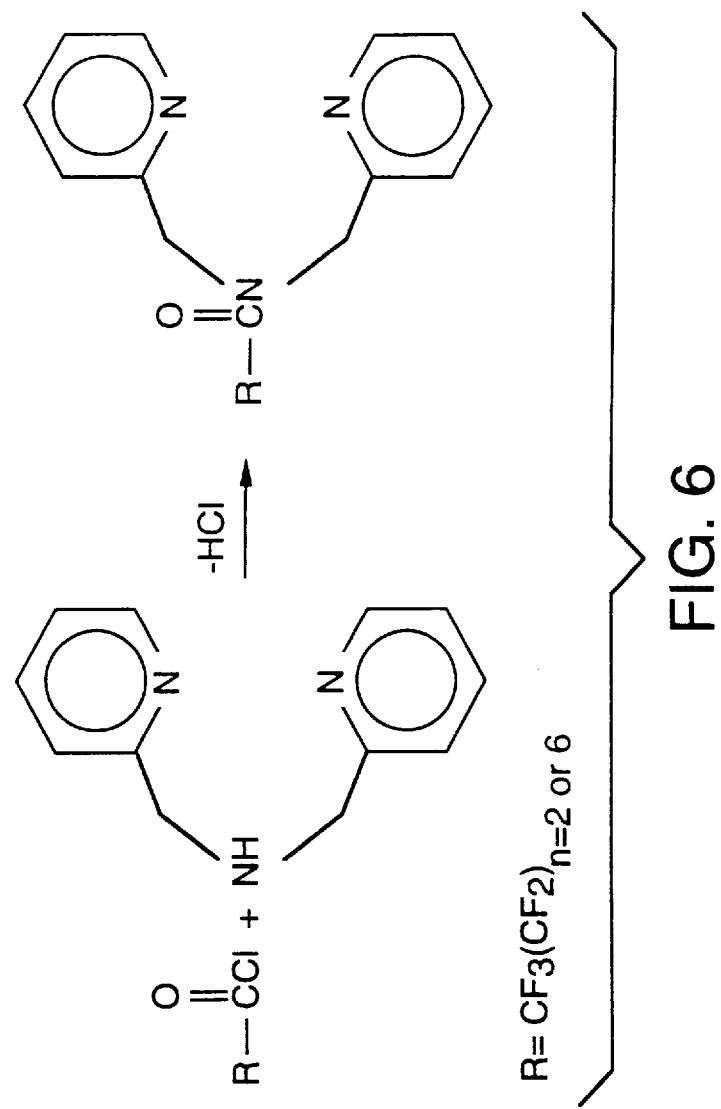
FIG. 6 illustrates a typical synthesis of the fluroalkyl bis(picolyl amine) chelating agent.

In a typical synthesis of the fluoroether bis(picolyl amine) chelating agent (see FIG. 6), 23 mmoles of the acid chloride (10.0 g of perfluorooctanoyl chloride or 5.3 g of perfluorobutanoyl chloride) were dissolved in 20 ml of perfluoroheptane (3M Performance Fluid 5070) under nitrogen in oven-dried glassware. This solution was added dropwise to a solution of 23 mmoles (4.6 g) of bis(picolyl amine) in 20 ml of anhydrous hexane while stirring vigorously under nitrogen at room temperature. After one hour of stirring, PolyDMAP (Reilly Industries), was added to the reaction mixture and temperature increased to 50° C. After an additional 24 hours of stirring, the mixture was filtered to remove the PolyDMAP and rotovaped at 70° C. to remove the solvents. The FT-IR showed the shifting of the carbonyl peak from 1803 $cm^{-1}$ (an acid chloride) to 1690 $cm^{-1}$ (amides) respectively for the perfluorooctanoyl and perfluorooctanoyl functional bis(picolyl amine).

b. Fluoroether-Spacer-Picolyl Amine

Figure 7:
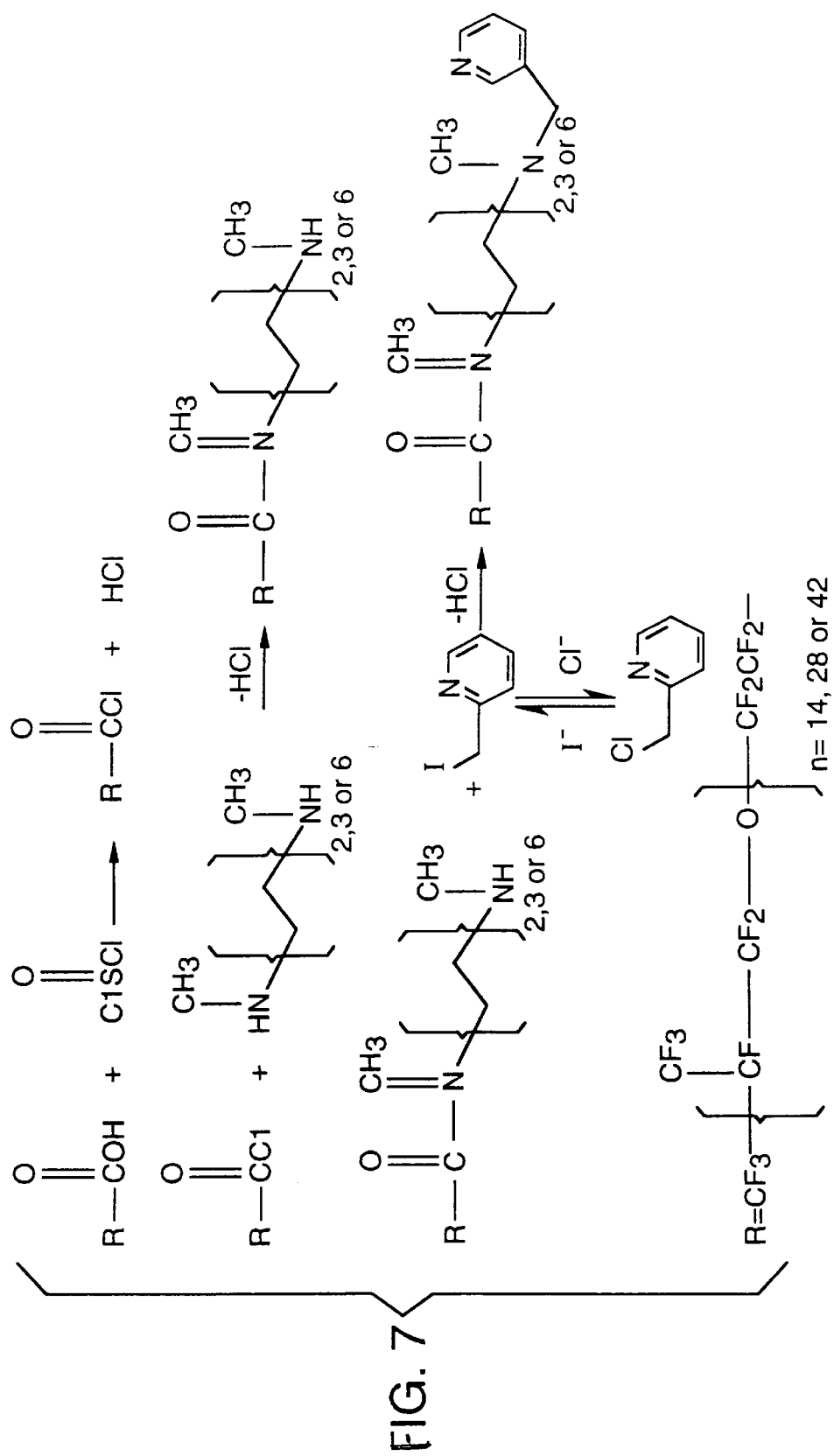
FIG. 7 illustrate the synthesis of the spacer-equipped picolyl amine chelating agents involving two steps.

Synthesis of the spacer-equipped picolyl amine chelating agents involves two steps, as shown in FIG. 7. In the first step a diamine, which serves as the spacer, is attached to the fluoroether tail. In a typical synthesis, 30 g (12 mmoles) of the Fluoroether acid chloride is dissolved in 40 ml of perfluoroheptane and added dropwise to a solution of 24 mmoles of the diamine (2.1 g of N,N'-Dimethyl-1, 6-hexanediamine) in 20 ml of anhydrous hexane under nitrogen. After an hour of mixing at room temperature, PolyDMAP was added and stirring continued for another 24 hours at 50° C. After removal of PolyDMAP by filtration, the solvents were removed by heating to 70° C. under vacuum and the product was washed with acetone several times. The FT-IR spectrum indicated the completion of the reaction by the shifting of the carbonyl peak from 1808 $cm^{-1}$. On the proton NMR, a new peak corresponding to the aminic proton appears ($\delta$=2.6 ppm) on all three spectra. On the fluoroether ethyl aminomethyl, three multiplets ($\delta$=1.8, 2.2 and 3.1) and a singlet ($\delta$=3.6) corresponding to the aldyl protons appear. On the fluoroether propyl aminomethyl, four multiplets ($\delta$=1.5, 1.8, 2.2, 3.1) and a singlet ($\delta$=3.5) appear and on the fluoroether hexyl amine a group of multiplets appear ($\delta$=1.2–2.4 and $\delta$=2.8–3.8 ppm).corresponding to the alkyl protons.

In the second step the chelating head, picolyl amine, is attached to the spacer-equipped fluoroether tail by the reaction of an alkyl chloride with an amine. In a typical synthesis, a solution of 8 mmoles of the spacer-equipped fluoroether (20 g), 32 mmoles 2-picolyl chloride hydrochloride (5.3 g), 6 mmoles of sodium iodide (1 g), 30 ml of 1,1,2 Trichloroethane and 50 ml of absolute ethanol were stirred at reflux temperature (sodium iodide is added for the in situ generation of picolyl iodide, which is a more reactive agent towards amines than the picolyl chloride). After 24 hours of stirring at the above conditions, 120 mmoles of sodium (2.8 g) in 15 ml of anhydrous ethanol was added to neutralize the hydrochloric acid (present in the picolyl chloride hydrochloride and also generated by the reaction of the amine with the alkyl chloride). After refluxing for another 24 hours, the solution was filtered to remove the insoluble salts, and then heated to 75° C. under vacuum to remove the solvents. The product was extracted with perfluoroheptane and then washed with ethanol and acetone several times to remove any remaining unreacted reagents. On the FT-IR spectrum, the intensity of the alkyl bands (at 2424, 2473, 2764 and 2950 cm$^{-1}$) increase and the amide peak shifts slightly to 1687 cm$^{-1}$. The NMR spectrum, new peaks appear corresponding to the aromatic protons ($\delta$=6.3, 6.8 and 8.0 for fluoroether ethyl picolyl amine, $\delta$=5.9, 6.3 and 7.9 for fluoroether propyl picolyl amine and $\delta$=5.9, 6.3 and 7.9 for fluoroether hexyl picolyl amine.

Phase Behavior

The phase behavior studies were performed using a high pressure variable volume view cell (D. B. Robinson and Associates), shown in FIG. 4. The procedure used in the phase behavior experiments was discussed hereinabove.

Extractions

Figure 8:
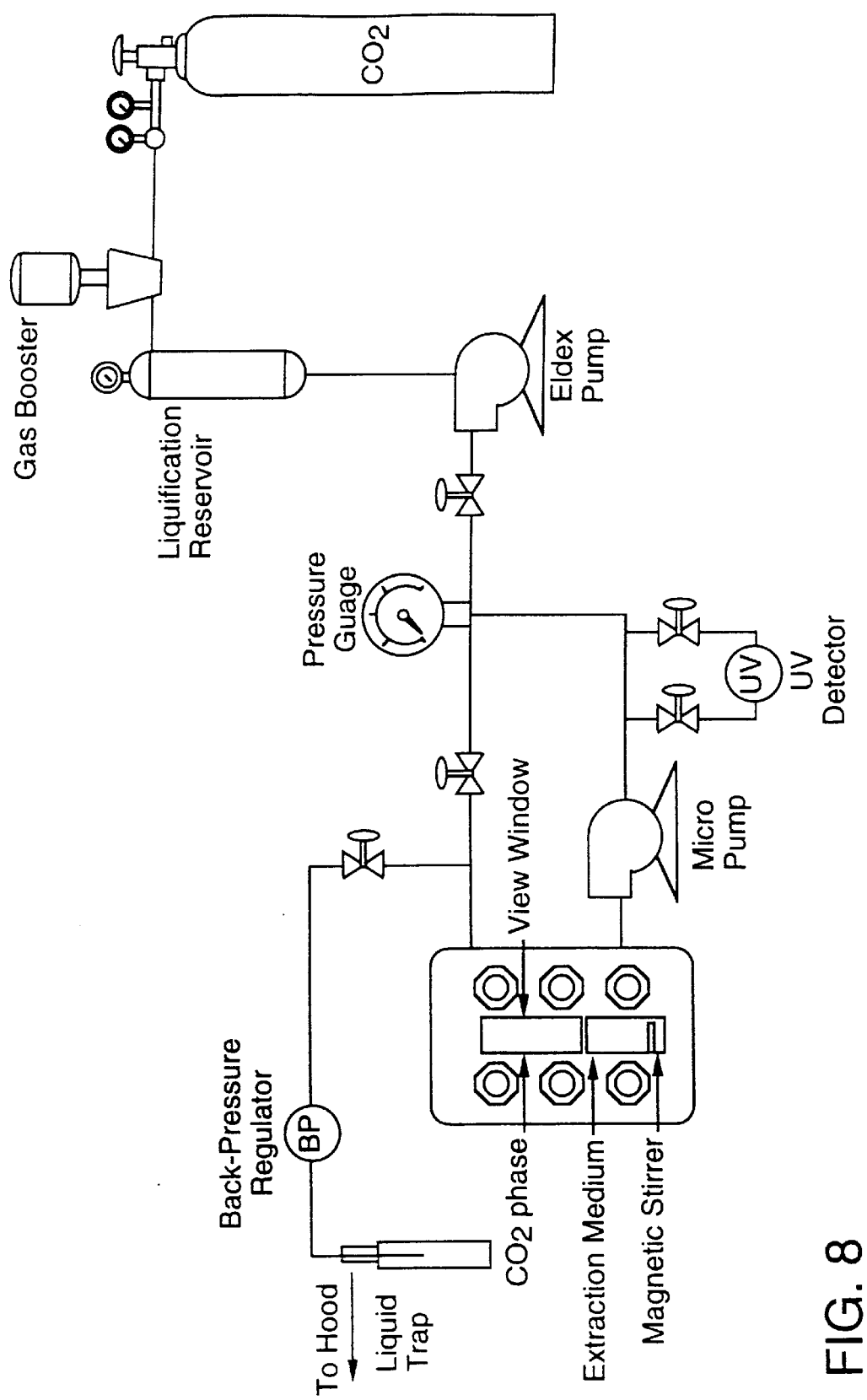
FIG. 8 discloses a high pressure extraction apparatus.

Extractions were performed using a high pressure extraction apparatus constructed at the University of Pittsburgh and shown in FIG. 8. The high pressure extractor is rated to 5000 psi and allows for constant recirculation and stirring of the sample. Two separately designed extraction cells allow for extraction of liquid and solid samples. An on-line high pressure UV detector is used for real time monitoring of the extraction progress and a back pressure regulator is used for continuous wash at the desired pressure at the end of the extraction.

After the extraction, the samples are analyzed using atomic absorption spectroscopy (Perkin Elmer Model 2380). In case of liquid samples, the only preparation required is a dilution (if necessary) to lower the sample concentration to the linear range for the given metal. Solid samples require a digestion into 1:1 HNO$_3$:Deionized H$_2$O by heating the sample and the acid solution to 100° C. for an hour while stirring vigorously. Subsequent dilutions with deionized water are made if necessary. The concentration of samples and blanks is determined by comparing their absorbance reading to a calibration curve constructed using known standards. EPA method SW846 was used to determine the minimum detection limit of the instrument for mercury (3.1 ppm) and lead (0.3 ppm) to assure the validity of the results.

Phase Behavior

Typically, one would prefer to minimize the molecular weight of a chelating agent to minimize the mass required to perform a particular extraction. However, in the case of the highly CO$_2$-soluble chelating agents described in this and preceding papers, increases to the molecular weight of the CO$_2$-philic tail can dramatically lower the pressure required for solubilization at a given concentration, which would lower both capital and operating costs for a full-scale process. Further, as shown by the results in FIG. 12, variations in the nature of the CO$_2$-philic group can also significantly affect the solubilization pressure.

Figure 9:
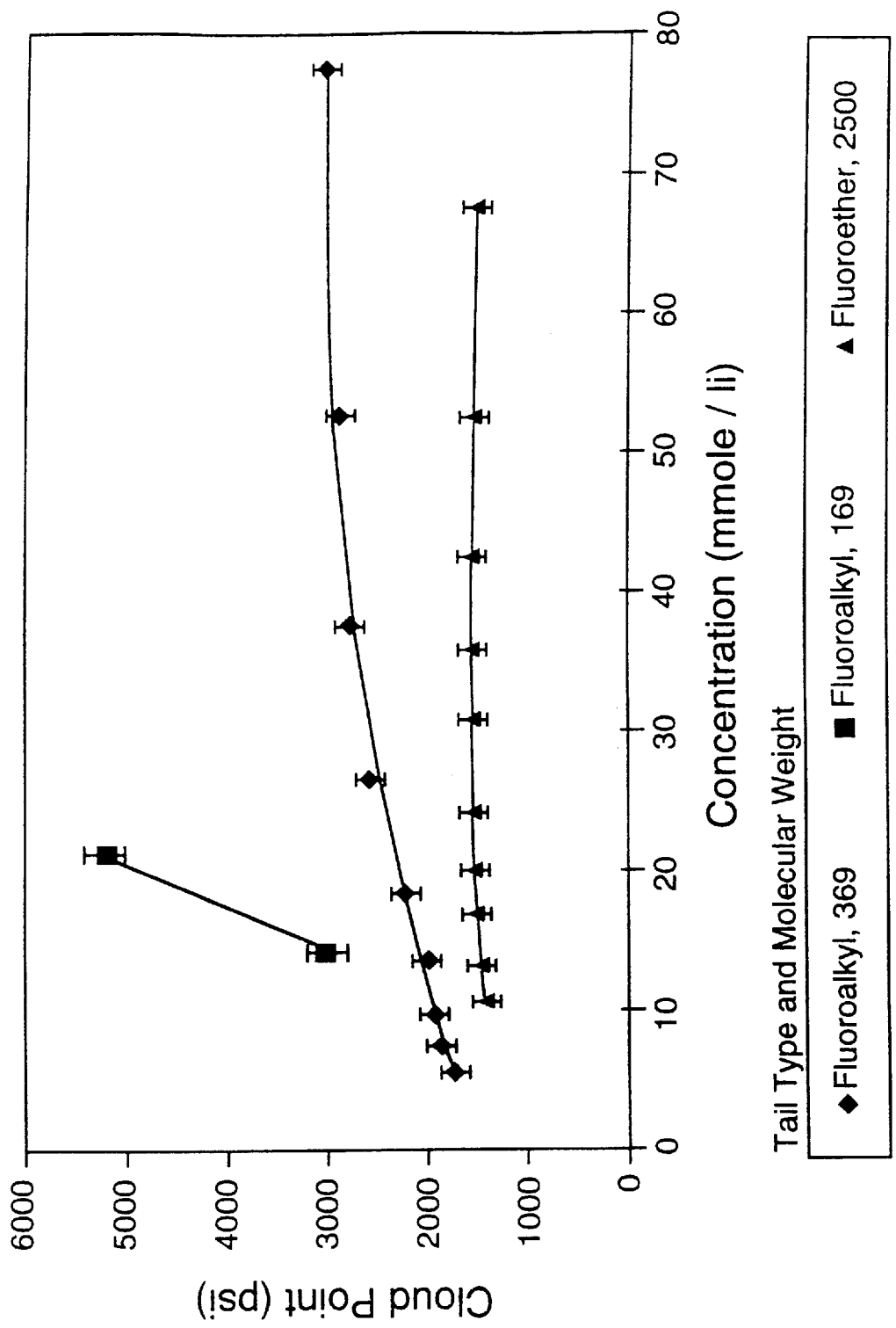
FIG. 9 illustrates that variations in the nature of the $CO_2$-philic group can affect the solubilization pressure.

As shown in FIG. 9, the agents functionalized with fluoroalky tails generally exhibit higher solubilization pressures (cloud points) than those incorporating fluoroether tails. However, it must be emphasized that the chain length for the fluoroether tails is significantly greater than that of the fluoroalkyl, which will contribute to the cloud point differences. In previous work, we have shown that contrary to the case of the phase behavior of a series of analogous materials, increases to the molecular weight of such amphiphilic molecules (CO$_2$-philic/CO$_2$-phobic) can decrease cloud point pressures, when the increase is confined to the CO$_2$-philic portion of the material. This latter effect can also be seen in FIG. 9, where an increase to the fluoroalkyl tail length from 169 to 369 decreases the cloud point pressure by 1000 to 3000 psi, depending upon concentration. Thus, although increasing the tail length increases material costs, it lessens process costs owing to a reduction in operating pressure.

Figure 10:
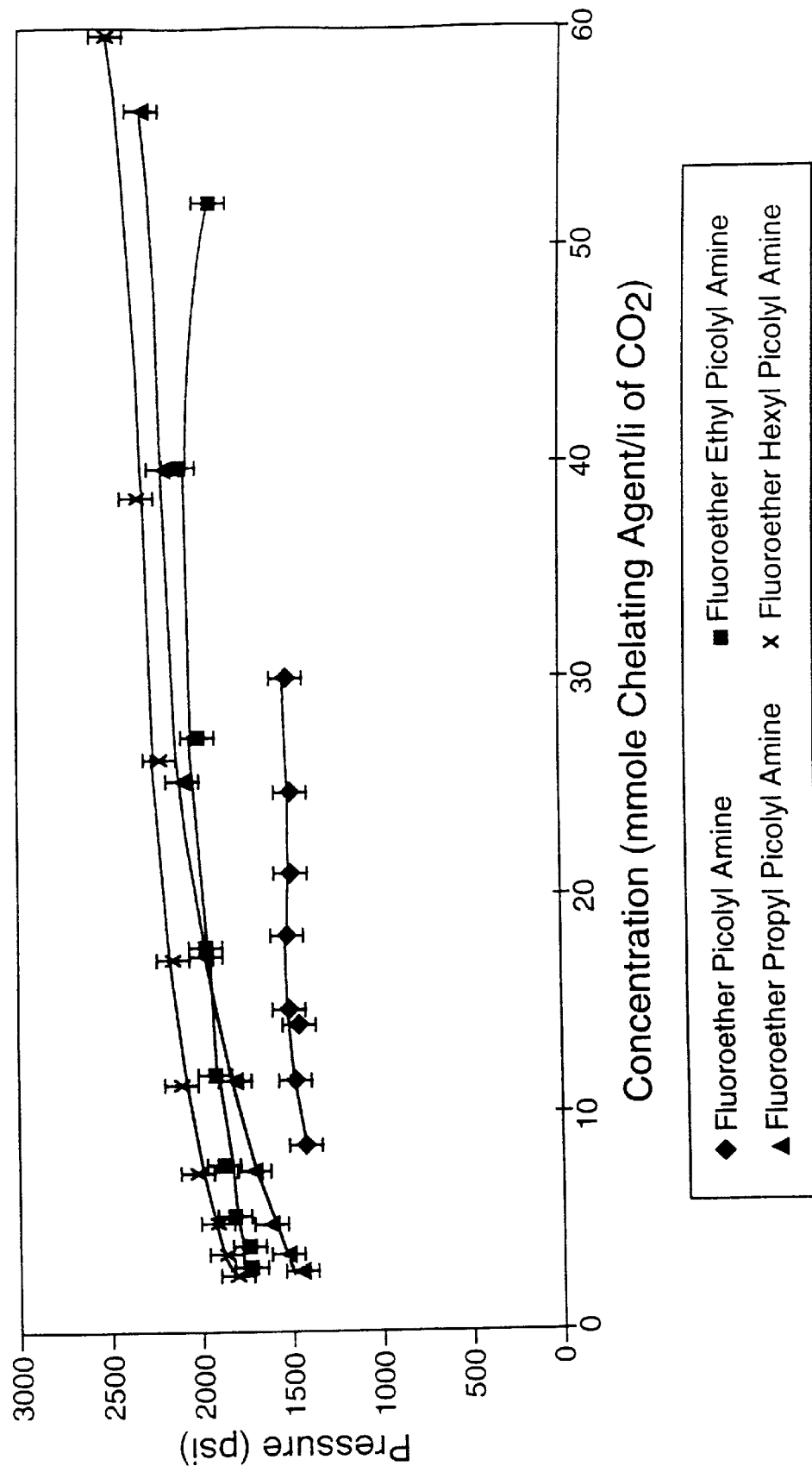
FIG. 10 discloses that the phase behavior of the agents is not effected significantly by the presence of the spacers.
Figure 11:
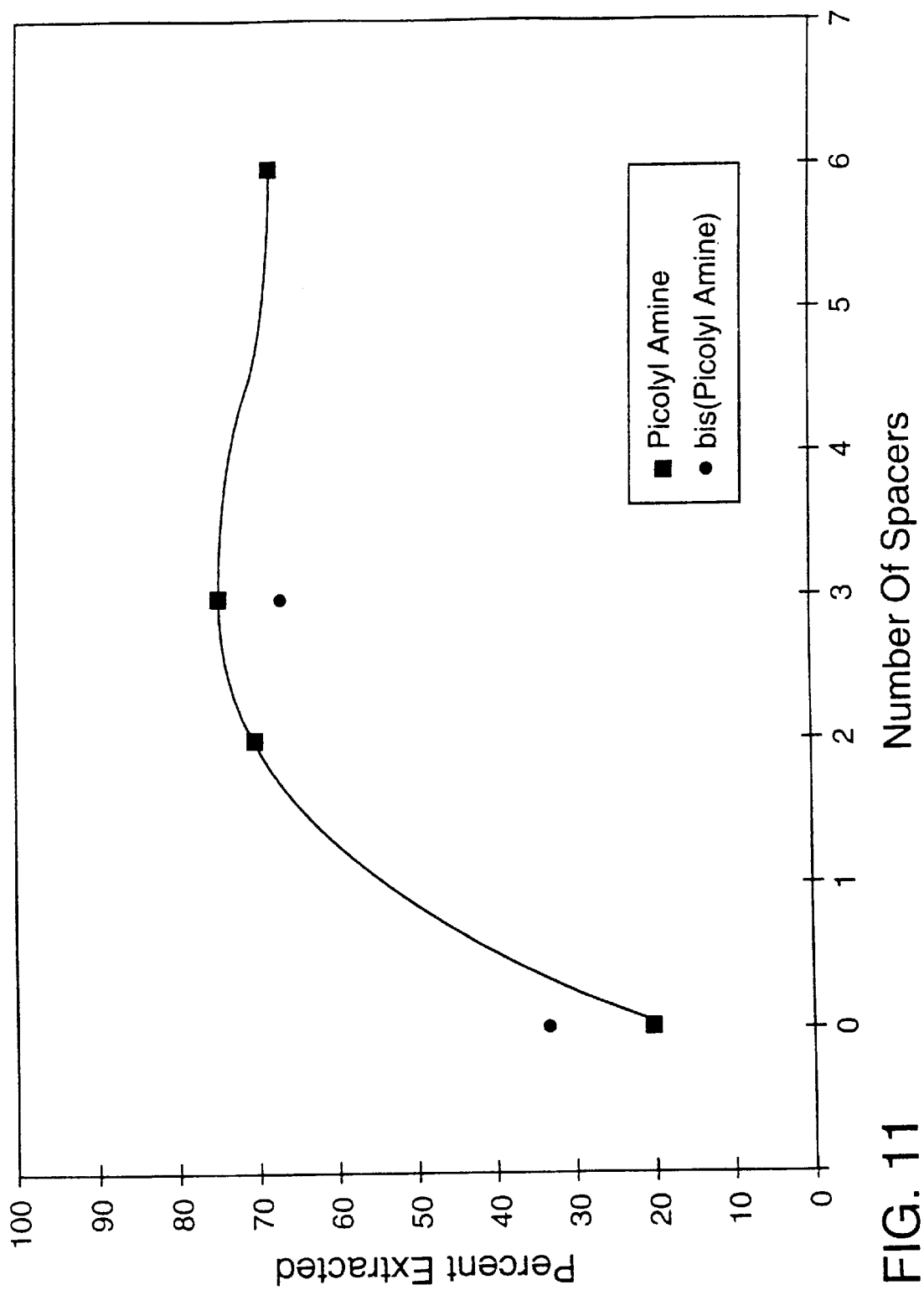
FIG. 11 discloses that the extracting efficiency for lead increases significantly upon adding an alkyl spacer of two carbons.
Figure 12:
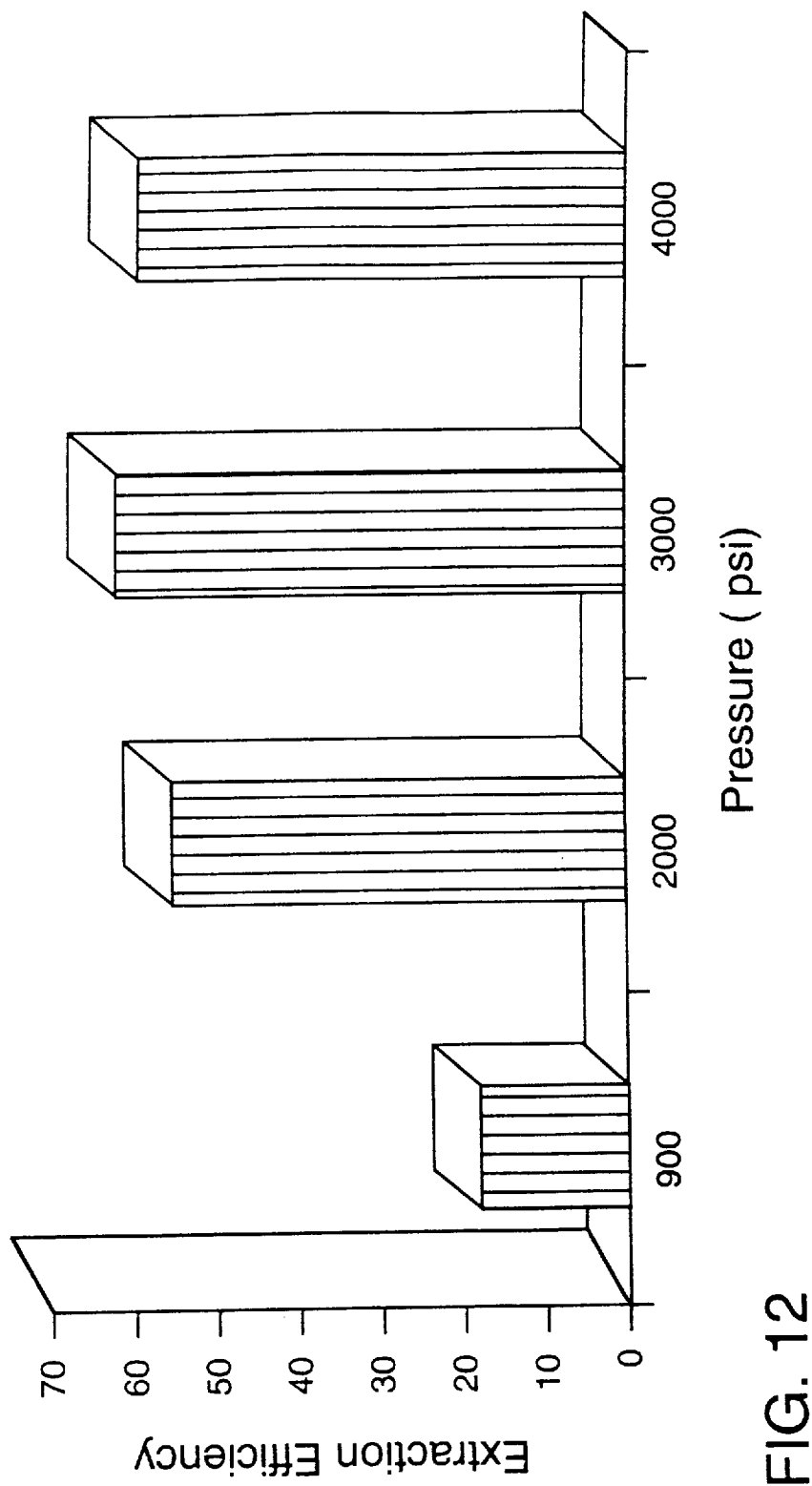
FIG. 12 illustrates the efficiency of fluoroether dithiocarbamate chelating agent for arsenic is not a function of pressure at 2000 psi and above.

The results of the phase behavior study of some fluoroether picolyl amine and bis(picolyl amine) chelating agents with and without alkyl spacers are shown in FIG. 10. As expected, the addition of the alkyl spacers increases somewhat the CO$_2$-phobic characteristic of the molecule and therefore raises its cloud point curve slightly. Further a direct relation between the length of the alkyl spacer and the increase in the cloud point curve is observed. Nevertheless, the effect of the alkyl spacers upon the phase behavior of the agents is, in general, relatively small Mitigation of the Effect of the Electron-Withdrawing Tail It has previously been observed that both the picolyl and bis(picolyl) amine chelating agents (fluoroether-functional) would extract almost all (greater than 90%, 2000 ppm initial loading, 1.5 ratio of chelating agent to metal, 1500 psi CO$_2$ pressure) of the mercury from a spiked sample of laboratory sand, extraction of lead under the same conditions was significantly poorer (20 to 30% of the lead extracted). Further, we observed that use of a silicone-functional chelating agent would allow greater than 90% of the lead to be extracted, albeit at much higher pressures (cloud point pressures for the silicone-functional materials are much higher than the analogous fluoroether-functional materials. Thus, the strongly electron-withdrawing tail of the picolyl and bis(picolyl amine) chelating agents was serving to partially deactivate the chelating head group, and that this effect was much more significant for lead than for mercury (suggesting stronger binding of mercury to the picolyl amine groups than lead). To check this, we synthesized several agents where the head group was separated from the fluoroether tail by alkyl spacers of various lengths, then performed extractions as before. As seen in FIG. 11, the phase behavior of the agents is not effected significantly by the presence of the spacers. However, as shown in FIG. 12, the extraction efficiency for lead increases significantly upon adding an alkyl spacer of 2 carbons. Increases to the spacer length beyond 2 carbons do not improve the extraction efficiency significantly. Results for bis(picolyl amine) chelating agents are similar to those for picolyl amine.

Effect of Pressure on Extraction Efficiency

It was expected that the pressure would affect the efficiency of the extraction insofar as pressure regulates the solubility of the chelating agent and the metal chelate, it has been shown hereinabove that the phase behavior of a metal chelate in CO$_2$ can be quite different from that of the parent chelating agent, and that identity of the metal also influences the cloud point loci). As shown by results in FIG. 12, this is apparently the case, as the extraction efficiency of fluoroether dithiocarbamate chelating agent for arsenic (from sand, pressure=2000 psi, 1.5 moles chelating agent per mole of metal, 2000 ppm initial loading of arsenic), is not a function of pressure at 2000 psi and above, falling off rapidly at pressures below the cloud point (=1300 psi) of the system. Although it would appear odd at first that one can actually extract nearly 20% of the metal at 900 psi, it must be remembered that while the system will phase separate at pressures below the cloud point, the dilute phase will indeed contain chelating agent, albeit at relatively low levels. Thus, flushing the system with pure CO$_2$ (as is the final step in our extraction procedure) will continually solubilize a certain amount of chelate, even at low pressures. It is thus likely that we could eventually push the extraction efficiency for the 900 psi run to equal that of the 2000 psi run, if enough carbon dioxide were moved through the extraction cell.

Effect of Molar Ratio of Chelating Agent to Metal

Figure 13:
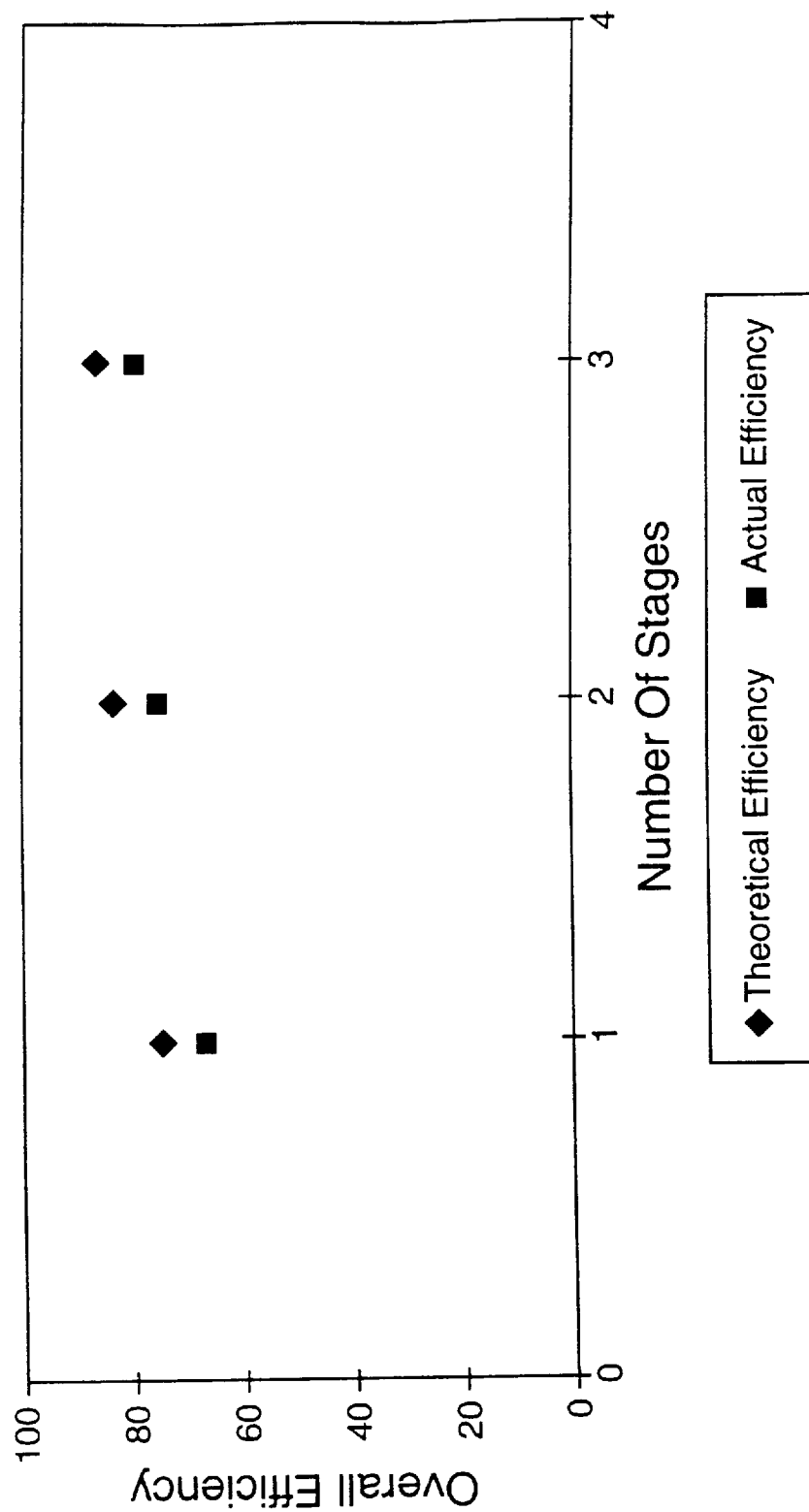
FIG. 13 illustrates the results of a series of arsenic extraction from sand performed with varying initial molar ratios of chelating agent to metal.

FIG. 13 depicts the results of a series of arsenic extractions from sand performed with varying initial molar ratios of chelating agent (the fluoroether dithiocarbamate) to metal. Increasing the molar ratio of chelating agent to metal from 1 to 3 results in about a 20% increase in extraction efficiency. But, as expected, further increases to this ratio result show diminishing returns, with only a 7% increase in extraction efficiency when the ratio is increased from 3 to 6.

Assuming that equilibrium has been established at the end of the extraction period, an expression can be derived to predict the theoretical yield for extractions under different conditions (varying chelating agent to metal ratio, varying number of stages, . . . ) Representing the metal as $M^+$, the chelating agent as $CA^-$ and the chelate complex as MCA, we have the equilibrium:

$$M+CA^- \rightarrow MCA$$

If we define the equilibrium constant K as:

$$K = \frac{[MCA]_1}{[M^+]_1 [CA^-]_1}$$

where $[MCA]_1$, $[M^+]_1$ and $[CA^-]_1$ are the concentrations of chelate complex, metal ion and chelating agent at equilibrium, respectively, then:

$$[MCA]_1 = K[M^+]_1[CA^-]_1$$

Based on a mass balances on total amount of metal and chelating agent, we have the two following equations:

$$[M^+]_1 = [M^+]_0 - [MCA]_1$$

$$[CA^-]_1 = [CA^-]_0 - [MCA]_1$$

from the two above equations:

$$[M^+]_1 = [M^+]_0 - [CA^-]_0 + [CA^-]_1$$

from definition of equilibrium constant:

$$[CA^-]_1 = \frac{[CA^-]_0}{1 + K[M^+]_1}$$

substituting this into the expression for $[M^+]_1$, followed by algebraic rearrangement, ultimately leads to an expression for the remaining metal in the matrix as a function of the initial metal concentration, the initial chelating agent concentration, and the equilibrium constant, as shown below:

$$[M^+]_1 = [M^+]_0 - [CA^-]_0 + \frac{[CA]_0}{1 + K[M^+]_1}$$

$$K[M^+]_1^2 + (1 - K[M^+]_0 + K[M^+]_0)[M^+]_1 - [M^+]_0 = 0$$

$$[M^+]_1 = \frac{K[M^+]_0 + K[CA^-]_0 - 1 \pm \sqrt{K^2([M^+]_0 - [CA^-]_0)^2 + 2K([M^+]_0 + [CA^-]_0) + 1}}{2K}$$

The value for K was chosen to provide the best fit of the experimental data in FIG. 14; this value of the equilibrium constant was subsequently used to predict the result of a multi-stage extraction below.

Multiple Stage Extractions

A series of arsenic extractions were performed using a fluoroether dithiocarbamate chelating agent. In each case the molar ratio of the total amount of chelating agent to the metal ion present in the sand was 3.0; here a single-pass extraction using the full charge of chelating agent was compared to several n-stage extractions where the chelating agent charge for each stage equaled the full charge divided by n. The derivation of the residual metal concentration, as a function of initial concentrations and equilibrium constant, can naturally be used to predict the extraction efficiency of the multi-stage extraction described above.

Figure 14:
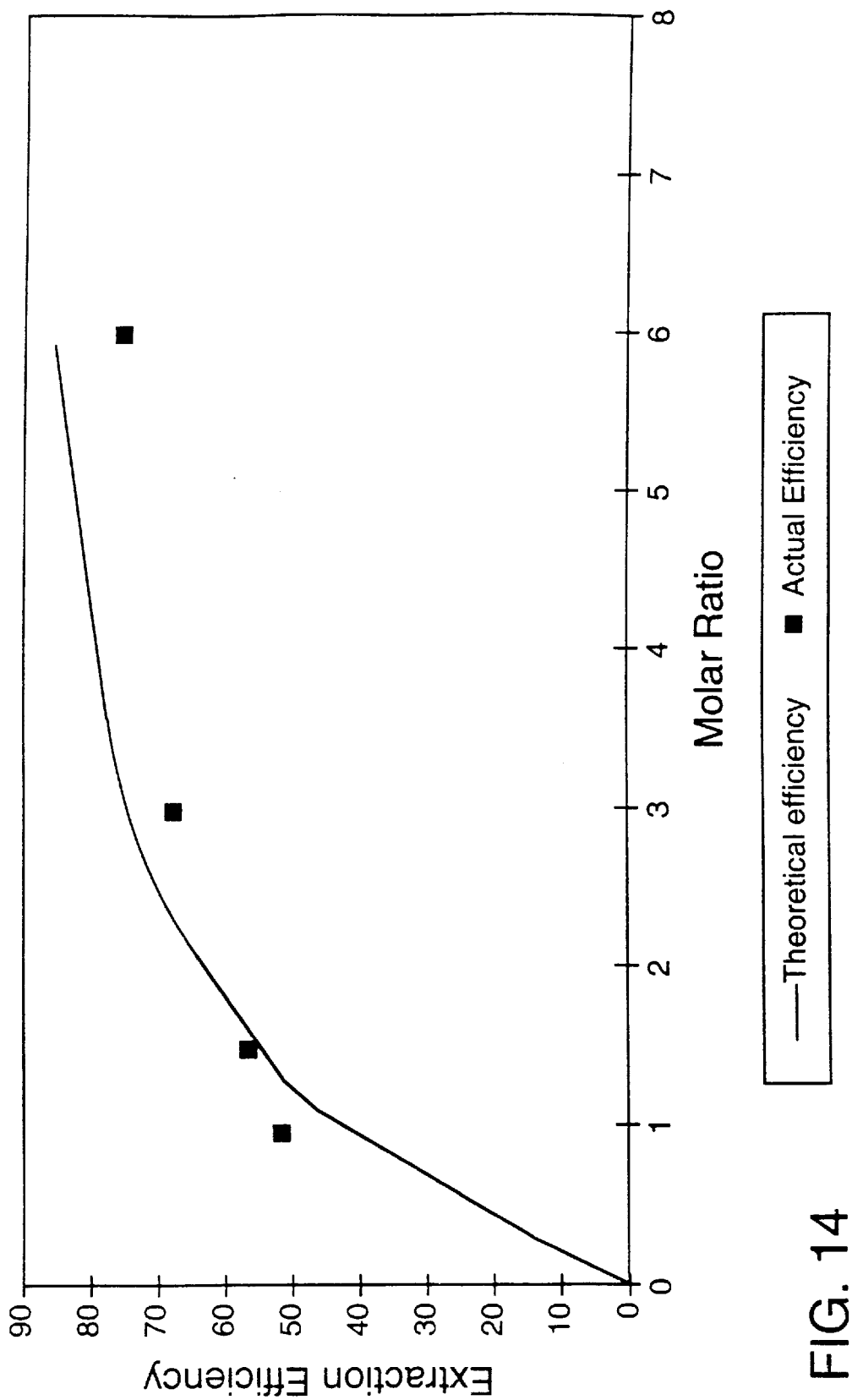
FIG. 14 illustrates both the theoretical and experimental increase in extraction efficiency with increasing the number of extraction stages.

FIG. 14 shows both the theoretical (using the K value from the molar ratio data) and experimental increase in extraction efficiency with the increasing number of stages. Note that if one desires an extraction efficiency of 75%, one can either employ a single stage extraction using a 6:1 molar ratio of agent to metal, or a 2-stage extraction using a 3:1 ratio. The optimum arrangement will depend upon material costs, recyclability of the chelating agent, and process costs.

The Matrix Effect

Figure 15:
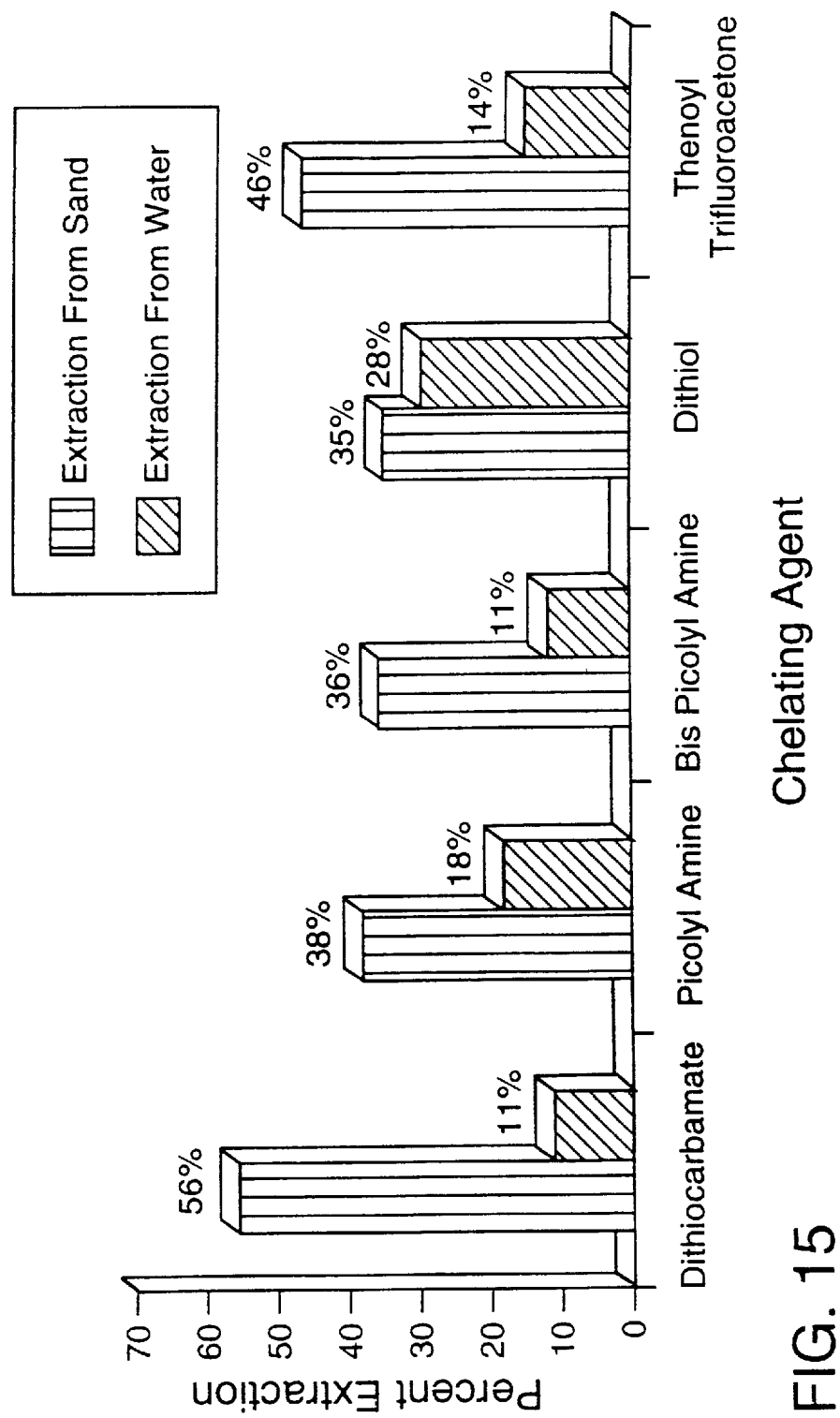
FIG. 15 illustrates the result of studies on the effect of matrix and low pH effect on extraction efficiency.

Extraction efficiencies as high as 98% for thenoyl trifluoroacetone and as high as 85% for fluoroether dithiocarbamate in extraction of iron from water into $CO_2$ are reported above. These results were surprisingly good considering the fact that under the extraction conditions, (2000 psi and room temperature) the pH of the water solution drops to 3 or lower (due to dissolution of $CO_2$ in water and subsequent $H_2CO_3$ formation and disassociation), which can be an unfavorable extraction condition for certain chelating agents. FIG. 15 shows the results of further studies on the effect of matrix and the low pH effect on extraction efficiency. Several arsenic extractions from sand were performed keeping pressure, molar ratio of chelating agent to metal, temperature, extraction time and wash time constant. The concentration of arsenic in the sand extractions was 1.0 milliequivalent of arsenic per 100 g of sand (750 ppm) and in the water extractions 0.2 milliequivalent of arsenic per 100 ml of water (150 ppm). As the results in FIG. 15 disclose, the low pH causes a significant drop in the efficiency of all of the fluoroether functional chelating agents. The magnitude of this effect varies with metal and chelating agent type as shown hereinabove.

Effect of Interfering Ions

Figure 16:
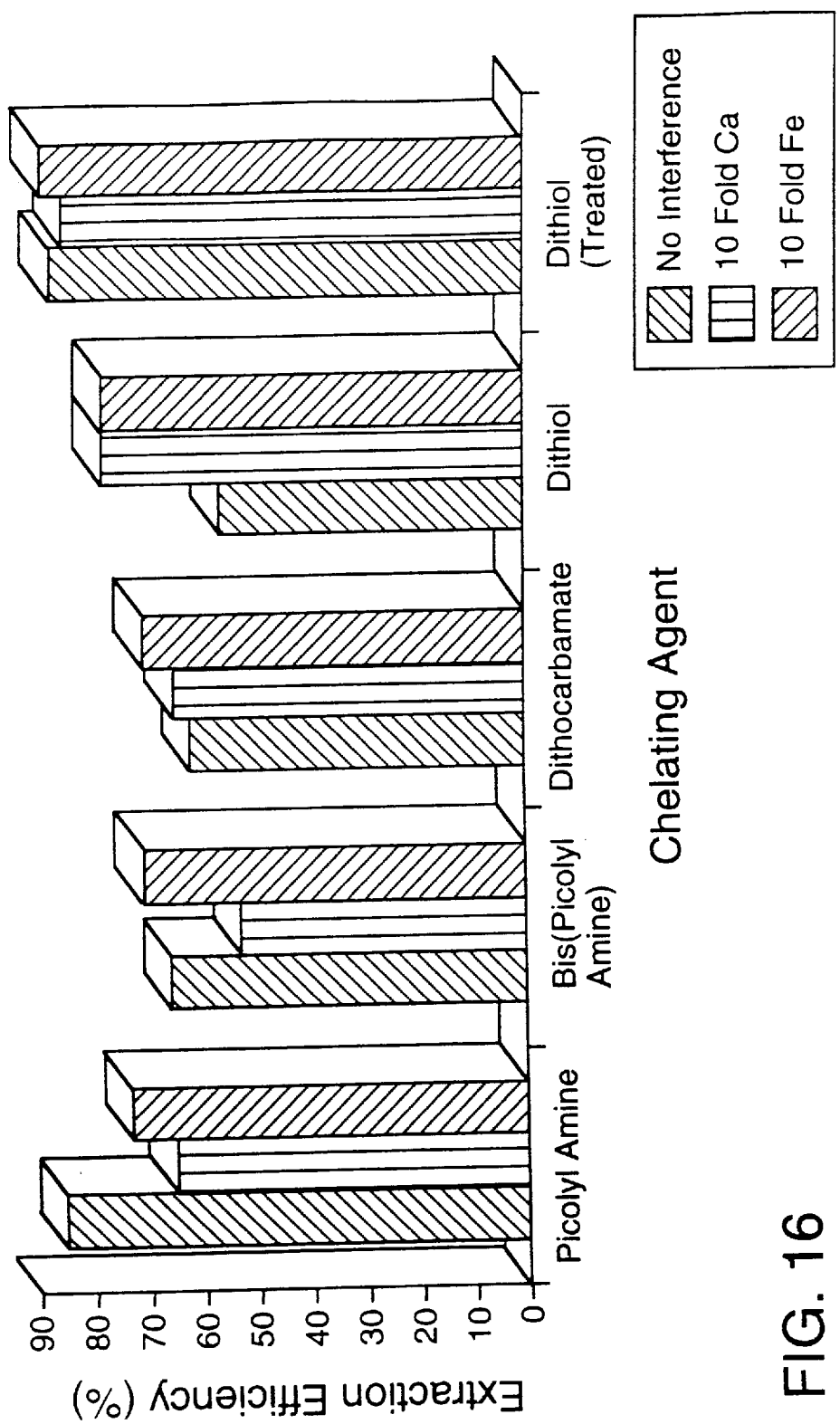
FIG. 16 discloses the effect of interfering ions.

Results of the studies on the effect of interfering ions are shown in FIG. 16. Extractions were performed from sand that contained 2000 ppm of mercury and 20,000 ppm of either iron or calcium. As was expected, fluoroether dithiol (treated with dithiothreitol to break the disulfide bonds) showed excellent selectivity towards mercury; the extraction efficiency in the presence of interfering ions is comparable to that of an extraction with no interfering ions. However, the fact that the other chelating agents show extraction efficiencies in presence of iron or calcium that are near (or in some cases better) than the efficiencies for extractions with no interfering ion present, leads to the belief that a factor other than selectivity of the chelating agents for mercury is operating here. It is possible that mercury is much less tightly bound to the sand than iron and calcium; this is supported by the fact that we have always observed the highest efficiency of any of the chelating agents in extraction of mercury (although mercury is volatile, treatment of the matrix with pure carbon dioxide (i.e., no chelating agent) at room temperature yields negligible amounts of extracted metal). It is also possible that iron or calcium are acting to break the disulfide bonds in the untreated dithiol chelating agents and thus are increasing its efficiency to near that of the dithiothreitol-treated dithiol agent.

Extraction Kinetics

Figure 17:
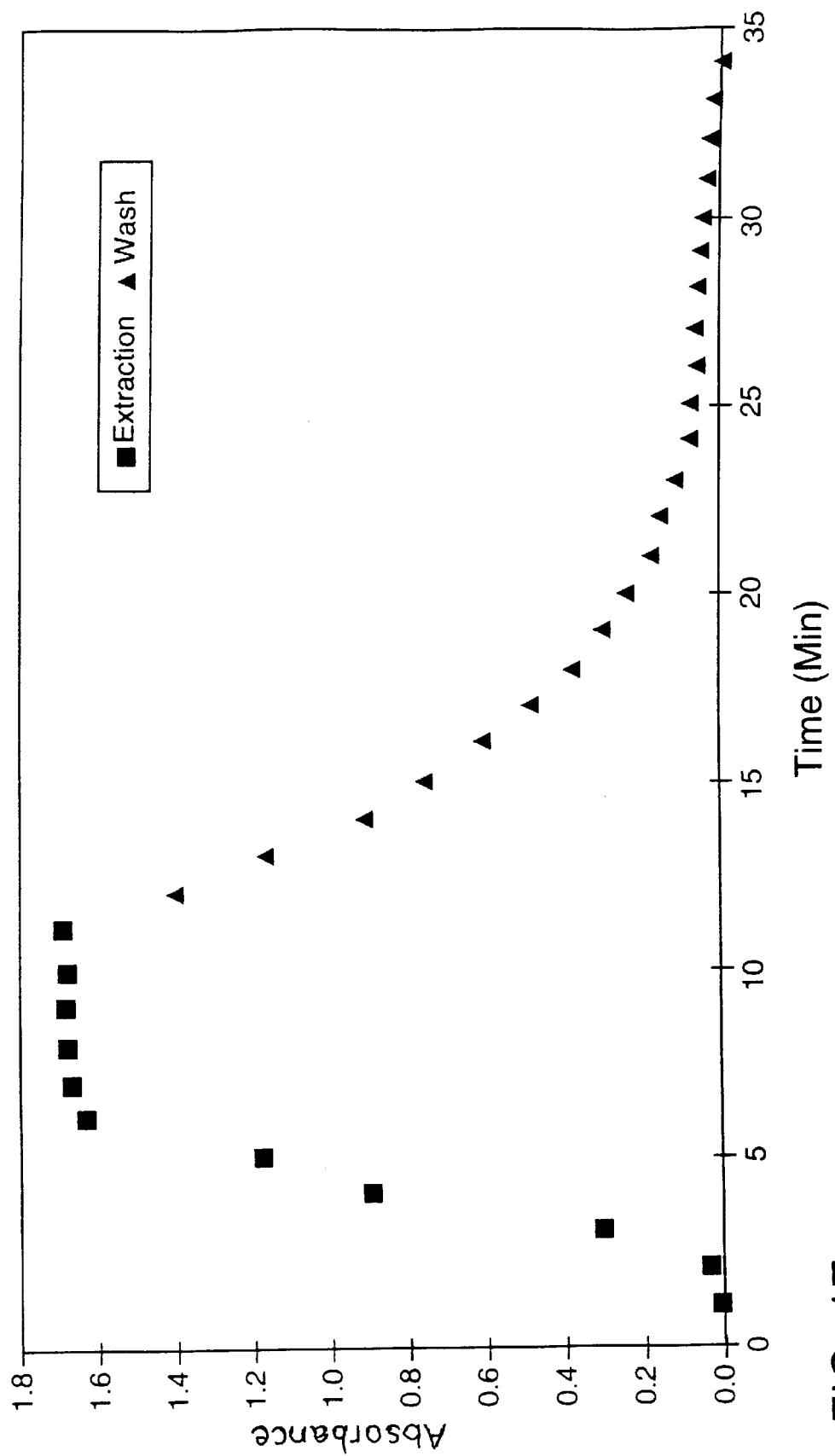
FIG. 17 discloses that for a typical extraction, equilibrium is attained in approximately six minutes [sand, pressure= 2000 psi, 1.5 moles chelating agent per mole of metal, 4000 ppm initial loading of calcium, circulating flow pump 25 ml/min.

Many metal chelates absorb strongly in the UV, while the chelating agent itself does not. This fact is made use of to observe the rate at which metal is extracted into $CO_2$ using UV model compounds. Of the case of a thenoyl trifluoroacetone chelate with calcium, the metal chelate absorbs strongly at 230 nm, and is thus readily observable using high pressure UV detector (see FIG. 8). As shown in FIG. 17, for a typical extraction (from sand, pressure=2000 psi, 1.5 moles chelating agent per mole of metal, 4000 ppm initial loading of calcium), equilibrium is attained in approximately six minutes at a circulating pump flow rate of approximately 25 ml/min. Following equilibrium, the recirculating pump is shut down and the piston pump activated, thus flushing the system with pure $CO_2$ reducing the metal chelate concentration exponentially, as would be expected in such a classical dilution situation.

In conclusion, the procedure for the synthesis of two fluoroalkyl bis(Picolyl Amine) chelating agents are outlined above. The phase behavior study shows that, due to its short length, the perfluorobutanoyl tail is not an efficient $CO_2$ solublilizing tail, but the perfluorooctanoyl tail provides high solubility at moderate pressure.

A two or three carbon spacer is sufficient for mitigation of the effect of the electron withdrawing tail on the electron-rich chelating head group.

Once the minimum pressure for solubilizing the chelating agent is reached, increasing the pressure has little or no effect on the efficiency of extraction.

Increasing the molar ratio of chelating agent to metal increases the extraction efficiency with the increase in the efficiency diminishing at higher chelating agent to metal ratios.

Extraction efficiency is improved using a higher number of stages and/or a higher chelate to metal ratio. For example, efficiency of extraction of arsenic from sand using fluoroether dithiocarbamate can be increased from approximately 67% (one stage, 3:1 chelate to metal ratio) to approximately 75% either by increasing the chelate to metal ratio (higher chelating agent cost) or by increasing the number of stages to two (higher operating costs).

The low pH of a mixture of water and high pressure $CO_2$, as previously discussed, hinders the extraction efficiency of some chelating agents significantly, while exercising little apparent effect on others.

Although the invention has been described in detail for the purposes of illustration, it is to be understood that such detail is solely for that purpose and that variations can be made therein by those skilled in the art without departing from the scope of the invention except as it may be limited by the claims.

What is claimed is:

1. A chelating agent suitable for forming coordinated complexes with a metal in liquid and supercritical carbon dioxide of covalently bonded (i) a chelating group selected from the group consisting of a dithiocarbamate group, a thiol group, and a picolyl amine group; (ii) a non-electron withdrawing spacer group selected from $(CH_2)_x$; and (iii) a $CO_2$ soluble functional group selected from $[CF_2CF_2O]_y$, $[CF_2O]_y$, $[CF_2]_y$ and $[CF_2(CF_3)FO]_y$, where x is selected to minimize the electron withdrawing effect of the $CO_2$ soluble functional group and x and y are each $\geq 3$ and are selected to achieve a chelating agent solubility of at least a $10^{-3}$ gram/gram $CO_2$.

2. The chelating agent of claim 1 wherein a solubility of at least $10^{-2}$ gm/gm $CO_2$ is attained at a temperature in the range of approximately 0° to 100° C.

3. The chelating agent of claim 2 wherein a solubility of at least $10^{-2}$ gm/gm $CO_2$ is attained at a temperature in the range of approximately 20° to 50° C.

4. The chelating agent of claim 1 wherein a solubility of at least $10^{-2}$ gm/gm $CO_2$ is attained at a pressure in the range of approximately 500 to 5000 psi.

5. The chelating agent of claim 4 wherein a solubility of at least $10^{-2}$ gm/gm $CO_2$ is attained at a pressure in the range of approximately 900 to 3000 psi.

6. A chelating agent suitable for forming coordinated complexes with a metal in liquid and supercritical carbon dioxide of covalently bonded (i) a chelating group comprising a dithiocarbamate group, (ii) a non-electron withdrawing spacer group selected from $(CH_2)_x$; and (iii) a $CO_2$ soluble functional group selected from $[CF_2CF_2O]_y$, $[CF_2O]_y$, $[CF_2]_y$ and $[CF_2(CF_3)FO]_y$, where x is selected to minimize the electron withdrawing effect of the $CO_2$ soluble functional group and x and y are each $\geq 3$ and are selected to achieve a chelating agent solubility of at least a $10^{-3}$ gram/gram $CO_2$.

7. The chelating agent of claim 1 wherein the chelating group is a dithiol group.

8. The chelating agent of claim 1 wherein the chelating group is a picolyl amine group.

9. The chelating agent of claim 1 wherein the fluorinated polyether group is a poly (hexafluoropropyler oxide) group.

10. The chelating agent of claim 1 wherein the fluorinated alkyl group is a perfluorohexyl group.

11. The chelating agent of claim 1 wherein the spacer group is $-(CH_2)_3$.

12. The chelating agent of claim 3 having the structure.

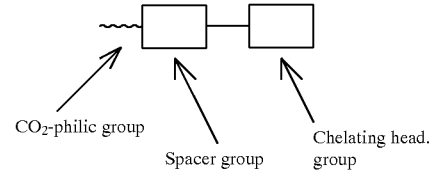

13. The chelating agent of claim 5 having the structure.

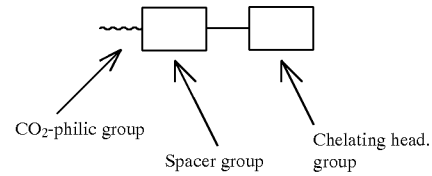

14. The chelating agent of claim 1 wherein arsenic extraction efficiency from sand is increased by having $\geq 2$ extraction stages.

15. The chelating agent of claim 1 wherein arsenic extraction efficiency from sand is increased by having >3:1 chelate to metal ratio.

16. A chelating agent suitable for forming coordinated complexes with a metal in liquid and supercritical carbon dioxide comprising three covalently bonded constituents, namely (i) a chelating group selected from the group consisting of a thiocarbamate group, a purine group, a thiofunctional purine group, a phosphate ester group and an iminodiacetic acid group; (ii) a non-electron withdrawing spacer group selected from $(CH_2)_x$; and (iii) a $CO_2$ soluble functional group selected from $[CF_2CF_2O]_y$, $[CF_2O]_y$, $[CF_2]_y$ and $[CF_2(CF_3) FO]_y$, wherein x and y are each $\geq 3$ and are selected to achieve a chelating agent solubility of at least a $10^{-3}$ gram/gram $CO_2$.

17. The chelating agent according to claim 16, wherein a solubility of at least $10^{-2}$ gm/gm $CO_2$ is attained at a temperature in the range of approximately 0° to 100° C.

18. The chelating agent according to claim 16, wherein a solubility of at least $10^{-2}$ gm/gm $CO_2$ is attained at a temperature in the range of approximately 20° to 50° C.

19. The chelating agent according to claim 16, wherein a solubility of at least $10^{-2}$ gm/gm $CO_2$ is attained at a pressure in the range of approximately 500° to 5000° C.

20. The chelating agent according to claim 16, wherein a solubility of at least $10^{-2}$ gm/gm $CO_2$ is attained at a temperature in the range of approximately 900° to 3000° C.

* * * * *

UNITED STATES PATENT AND TRADEMARK OFFICE
CERTIFICATE OF CORRECTION

| | |
|---|---|
| PATENT NO. | : 5,872,257 |
| APPLICATION NO. | : 08/831999 |
| DATED | : February 16, 1999 |
| INVENTOR(S) | : Eric Beckman and Alan J. Russell |

It is certified that error appears in the above-identified patent and that said Letters Patent is hereby corrected as shown below:

Column 1, line 9, before the heading "FIELD OF THE INVENTION", insert the following heading and paragraph:

-- GOVERNMENTAL INTEREST

This invention was made with government support under grant number 821781010 awarded by the U.S. Environmental Protection Agency (EPA). The government has certain rights in this invention. --

Signed and Sealed this

Thirtieth Day of September, 2008

JON W. DUDAS
*Director of the United States Patent and Trademark Office*